(12) United States Patent
Tribble et al.

(10) Patent No.: US 7,499,581 B2
(45) Date of Patent: Mar. 3, 2009

(54) VISION SYSTEM TO CALCULATE A FLUID VOLUME IN A CONTAINER

(75) Inventors: Dennis Tribble, Ormond Beach, FL (US); Abdul Wahid Khan, Lindenhurst, IL (US); John A. Adams, Escondido, CA (US)

(73) Assignee: ForHealth Technologies, Inc., Daytona Beach, FL (US)

( * ) Notice: Subject to any disclaimer, the term of this patent is extended or adjusted under 35 U.S.C. 154(b) by 809 days.

(21) Appl. No.: 11/055,545

(22) Filed: Feb. 10, 2005

(65) Prior Publication Data

US 2006/0178578 A1  Aug. 10, 2006

(51) Int. Cl.
  G06K 9/00   (2006.01)
  A61M 5/00   (2006.01)
  G01N 21/49  (2006.01)
  G01B 11/22  (2006.01)

(52) U.S. Cl. .................. 382/141; 382/128; 600/432; 356/134; 356/627; 250/577

(58) Field of Classification Search ............... 382/128, 382/141, 142; 600/432; 356/129, 134, 627; 250/577
See application file for complete search history.

(56) References Cited

U.S. PATENT DOCUMENTS

| | | | |
|---|---|---|---|
| 1,977,603 A * | 10/1934 | Weston | 73/293 |
| 2,118,229 A * | 5/1938 | Reynolds et al. | 73/747 |
| 2,303,154 A * | 11/1942 | Armstrong | 73/327 |
| 2,880,723 A | 4/1959 | Adams | |
| 2,981,432 A | 4/1961 | Flood | |
| 2,988,984 A | 6/1961 | Eckert | |
| 3,527,017 A | 9/1970 | Taylor et al. | |
| 3,736,933 A | 6/1973 | Szabo | |
| 3,774,603 A * | 11/1973 | McPhee | 604/246 |
| 3,835,897 A | 9/1974 | Gess | |
| 3,865,236 A | 2/1975 | Rycroft | |
| 3,880,211 A | 4/1975 | Gess | |
| 3,965,945 A | 6/1976 | Ross | |
| 4,058,121 A | 11/1977 | Choksi et al. | |
| 4,535,820 A | 8/1985 | Raines | |
| 4,605,851 A * | 8/1986 | Ometz et al. | 250/223 B |
| 4,624,148 A | 11/1986 | Averette | |
| 4,654,535 A * | 3/1987 | Wolske | 250/577 |
| 4,683,916 A | 8/1987 | Raines | |
| 4,691,231 A * | 9/1987 | Fitzmorris et al. | 348/127 |

(Continued)

OTHER PUBLICATIONS

U.S. Appl. No. 10/728,371, Osborne et al.

(Continued)

Primary Examiner—Matthew C Bella
Assistant Examiner—Anthony Mackowey
(74) Attorney, Agent, or Firm—Leason Ellis LLP

(57) ABSTRACT

Broadly speaking the present invention is directed to a system for calculating a volume of fluid that is disposed within a container. The system includes (1) an imaging device that captures and stores an image of at least the volume of fluid in the container; (2) a background disposed behind the container so that at least the volume of fluid in the container is disposed in front of the background; and (3) a processor that performs at least one operation on the stored image to calculate the volume of the fluid within the container.

38 Claims, 13 Drawing Sheets

U.S. PATENT DOCUMENTS

| | | | |
|---|---|---|---|
| 4,699,186 A | | 10/1987 | Palin et al. |
| 4,864,302 A | * | 9/1989 | Bowers ........................ 341/13 |
| 5,004,962 A | | 4/1991 | Fonss et al. |
| 5,062,828 A | * | 11/1991 | Waltz .......................... 73/327 |
| 5,229,074 A | | 7/1993 | Heath et al. |
| 5,256,154 A | | 10/1993 | Liebert et al. |
| 5,288,285 A | | 2/1994 | Carter |
| 5,341,854 A | | 8/1994 | Zezulka et al. |
| 5,356,393 A | | 10/1994 | Haber et al. |
| 5,363,885 A | | 11/1994 | McConnell et al. |
| 5,431,201 A | | 7/1995 | Torchia et al. |
| 5,451,528 A | | 9/1995 | Raymoure et al. |
| 5,463,228 A | * | 10/1995 | Krause ....................... 250/577 |
| 5,479,969 A | | 1/1996 | Hardie et al. |
| 5,523,560 A | * | 6/1996 | Manique et al. ......... 250/223 B |
| 5,597,530 A | | 1/1997 | Smith et al. |
| 5,651,775 A | | 7/1997 | Walker et al. |
| 5,669,599 A | | 9/1997 | Toh et al. |
| 5,704,921 A | | 1/1998 | Carilli |
| 5,769,086 A | | 6/1998 | Ritchart et al. |
| 5,805,454 A | | 9/1998 | Valerino |
| 5,884,457 A | | 3/1999 | Ortiz et al. |
| 5,899,889 A | | 5/1999 | Futagawa et al. |
| 5,911,252 A | | 6/1999 | Cassel |
| 5,914,272 A | * | 6/1999 | Dufresne et al. ............... 436/70 |
| 5,948,360 A | | 9/1999 | Rao et al. |
| 6,027,472 A | | 2/2000 | Kriesel et al. |
| 6,048,086 A | | 4/2000 | Valerino |
| 6,200,289 B1 | | 3/2001 | Hochman et al. |
| 6,226,081 B1 | * | 5/2001 | Fantone et al. ............ 356/239.6 |
| 6,315,760 B1 | * | 11/2001 | Sharp ......................... 604/189 |
| 6,343,690 B1 | | 2/2002 | Britton et al. |
| 6,685,678 B2 | * | 2/2004 | Evans et al. .................. 604/207 |
| 6,753,527 B1 | * | 6/2004 | Yamagishi et al. ...... 250/339.06 |
| 6,891,182 B2 | * | 5/2005 | Watari et al. ........... 250/559.19 |
| 7,408,632 B2 | * | 8/2008 | Moore ........................ 356/134 |
| 2001/0018937 A1 | | 9/2001 | Nemoto |
| 2002/0020459 A1 | | 2/2002 | Baldwin |
| 2002/0134923 A1 | * | 9/2002 | Watari et al. ................. 250/221 |
| 2002/0154809 A1 | * | 10/2002 | Yamagishi et al. ........... 382/142 |
| 2002/0198738 A1 | | 12/2002 | Osborne |
| 2004/0088951 A1 | | 5/2004 | Baldwin |
| 2005/0185184 A1 | * | 8/2005 | Moore et al. ................. 356/442 |
| 2006/0154327 A1 | * | 7/2006 | Bachur et al. .................. 435/34 |
| 2008/0137904 A1 | * | 6/2008 | Meredith et al. ............. 382/100 |

OTHER PUBLICATIONS

U.S. Appl. No. 10/728,364, Osborne et al.
U.S. Appl. No. 10/728,363, Osborne et al.
U.S. Appl. No. 10/426,910, Osborne et al.
U.S. Appl. No. 10/846,959, Wahid et al.

* cited by examiner

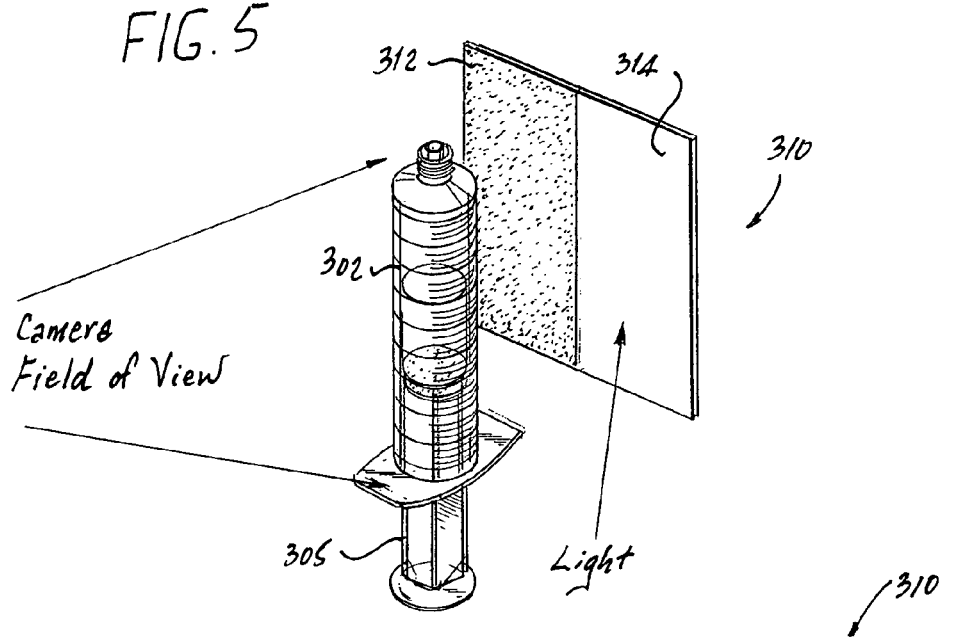
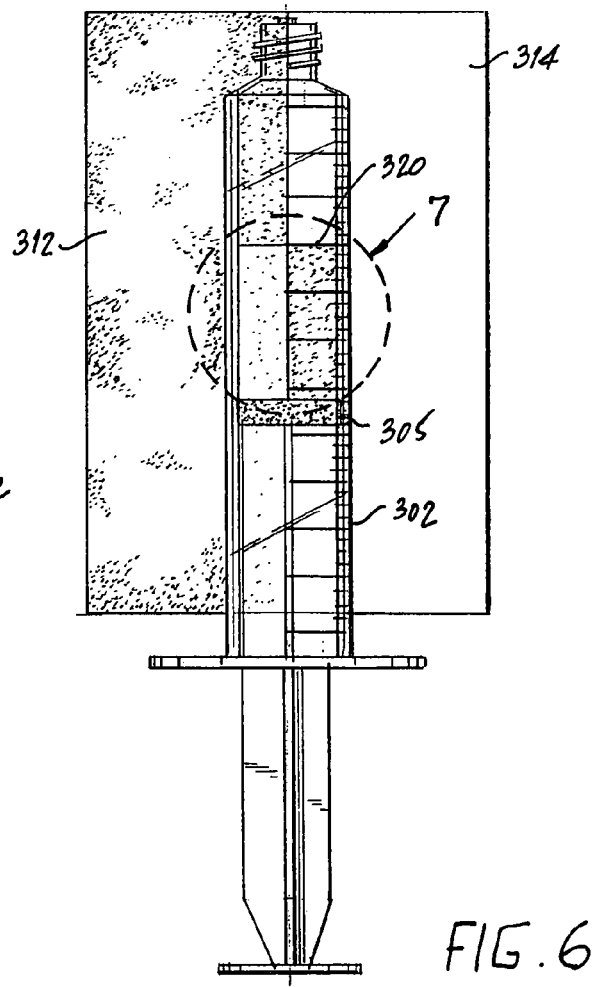
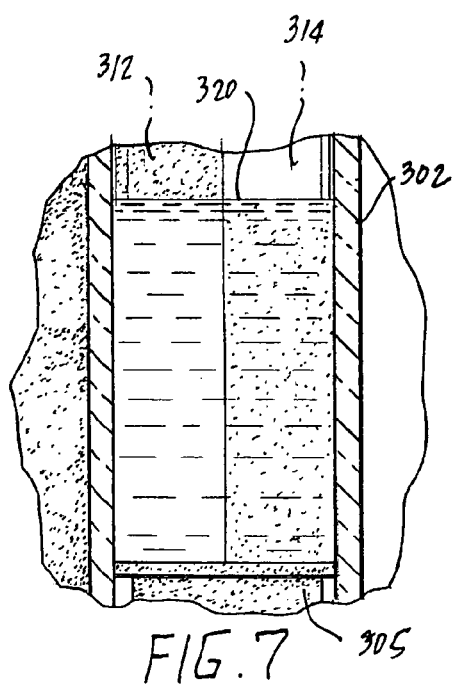

Calibration of Pixels to ml

VISION SYSTEM TO CALCULATE A FLUID VOLUME IN A CONTAINER

TECHNICAL FIELD

The present invention relates generally to a vision system, and more particularly, to a vision system that is configured to determine a volume of fluid in a container, and according to one embodiment, the present invention finds particular utility when it is used in combination with an automated medication preparation system that includes preparation of a unit dose of medication from a medication source and then delivery of the unit dose of medication to a product container, such as a syringe or the like.

BACKGROUND

In a wide number of settings, it is important to be able to accurately calculate the volume of a liquid that is contained in a container, such as glasswear. Existing techniques are cumbersome and very time consuming and are prone to error. For example, one technique is simply manual observation of the liquid and then using some type of graduation system to calculate the volume of the liquid. Other techniques involve using a measurement device which measures the liquid after it has been transferred from the container to the measurement device; however, in settings where precision is required, this technique is not that effective since some of the liquid may evaporate or be left behind. All of these techniques are not particularly suited for use in an automated system where a number of containers, such as product containers, are prepared by adding a prescribed volume of liquid and subsequently further processed, such as packaging of the products.

One particular industry that uses a considerable number of product containers is the medical and pharmaceutical industries. As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume. In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, including a large number of doses of medications that must be prepared daily. Traditionally, these doses have been prepared manually in what is an exacting but tedious responsibility for a highly skilled staff. In order to be valuable, automated systems must maintain the exacting standards set by medical regulatory organizations, while at the same time simplifying the overall process and reducing the time necessary for preparing the medications.

Because syringes are used often as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with one's hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

If the medication needs to be reconstituted, the medication initially comes in a solid form and is contained in an injectable drug vial and then the proper amount of diluent is added and the vial is agitated to ensure that all of the solid goes into solution, thereby providing a medication having the desired concentration. The drug vial is typically stored in a drug cabinet or the like and is then delivered to other stations where it is processed to receive the diluent. As is known, the drug vial typically includes a pierceable septum that acts as a seal and prevents unwanted foreign matter from entering into the drug vial so as to contaminate the contents thereof as well as keeping the contents safely within the interior of the drug vial when the drug is stored or even during an application. The septum is typically formed of a rubber material that can be pierced by a sharp transfer device to permit communication with the interior of the drug vial and then when the transfer device is removed the small piercing hole seals itself due to the material properties of the septum.

Typically, the medication is aspirated or otherwise withdrawn from the drug vial into a fluid conduit that can be in the form of a section of tubing or can be a cannula or a syringe. Unfortunately and as previously indicated, one of the difficulties in the filling process involves checking to see if the delivered volume of fluid is the correct amount since there are a number of reasons, such as the presence of foreign matter and mechanical malfunction, as to why the delivered volume of fluid can either be too great or too little compared to the intended delivery amount. When dealing with preparing medications, as well as other applications that involve a great degree of precision, it is important that the integrity of the fill not be jeopardized and as a result, it is a very time consuming and arduous task to confirm that the syringe or other type of container contains the correct amount of fluid.

What is needed in the art and has heretofore not been available is a system and method for automating the medication preparation process and more specifically, a safety and cost reducing feature that is capable of determining a characteristic of the syringe fill and more particularly, is capable of determining and checking the integrity of the syringe fill.

SUMMARY

Broadly speaking the present invention is directed to a system for calculating a volume of fluid that is disposed within a container. The system includes (1) an imaging device that captures and stores an image of at least the volume of fluid in the container; (2) a background disposed behind the container so that at least the volume of fluid in the container is disposed in front of the background; and (3) a processor that performs at least one operation on the stored image to calculate the volume of the fluid within the container.

In another aspect, a method for calculating a volume of fluid that is disposed within a syringe having a slideable plunger is provided and is defined by the following steps. A background is placed behind the syringe so that at least the volume of fluid is disposed in front of the background. The background has a black-side and an adjacent white-side with an interface edge formed therebetween, with the syringe being positioned along the interface edge such that approximately ½ of the syringe is associated with the black-side of the background and approximately the other ½ of the syringe is associated with the white-side of the background.

An image is captured and stored of at least the volume of fluid with a digital imaging device and at least one operation is performed on the stored image to calculate the volume of the fluid disposed within the container. In one exemplary embodiment and according to a first method of calculating the volume of liquid in the syringe, the operations include the steps of dividing the stored image into a black-side and a white-side that correspond to the black and white-sides, respectively, of the background and scanning the black and white-sides of the stored image. The scan measures a gray-scale value of scanned medium detected along a length of the syringe.

Feature vectors of the white-side scan and the black-side scan are plotted, with the plot having ascending gray-scale values along an x-axis and ascending pixel numbers along a y-axis that measures from a top to a bottom of the captured image. The feature vectors of the white and black-side scans are then low-pass filtered to form a low-pass filtered scan. Next, the white-side low-pass filtered vector is divided by the black-side low-pass filtered vector to form a ratio vector; and the ratio vector is plotted with ascending gray-scale values along an x-axis thereof and ascending pixel numbers along a y-axis thereof. The plot is analyzed for a point at which the ratio vector crosses 1 as measured on the x-axis which represents the air-liquid interface for the fluid in the container.

A position of the plunger is calculated by performing the steps of detecting a backside of the plunger; correcting the plunger position by subtracting an offset that corresponds to an actual thickness of the plunger; and calculating the volume of the fluid in the syringe based on the position of the air-liquid interface and the plunger position.

According to a second method of calculating the volume of liquid in the syringe, the above mentioned feature vectors are not divided but rather, the air/liquid boundary is determined using a top scan line (e.g., a white-side scan) and more specifically, a change in the slope of the top scan line is analyzed and when the change in slope of the top scan line exceeds a predetermined threshold, the air/liquid boundary is determined. Next, the air space volume is calculated using a $2^{nd}$ order polynomial and after calculating the actual plunger location, the plunger volume is determined using a $2^{nd}$ order polynomial. The actual volume of the liquid is thus calculated as being the plunger volume minus the air space volume.

The present invention thus provides an efficient, alternative system and method for precisely calculating a volume of liquid in the container that overcomes the disadvantages of the prior art devices. Importantly, the present system can be easily incorporated into an automated system, such as one where a number of liquid-containing product containers are produced by an automated process, so as to provide a vision detection system that can precisely calculate whether each product container has the correct volume of liquid.

Further aspects and features of the exemplary in-situ vision gauge disclosed herein can be appreciated from the appended Figures and accompanying written description.

BRIEF DESCRIPTION OF THE DRAWINGS

FIG. 5 is a perspective view of a syringe in front of a background that forms a part of the vision system of FIG. 2;

FIG. 6 is a front elevation view of the syringe in front of the background of the vision system;

FIG. 7 is a local view taken along the circle 7 of FIG. 6 showing an air/liquid interface in the syringe;

DETAILED DESCRIPTION OF PREFERRED EMBODIMENTS

Figure 1:
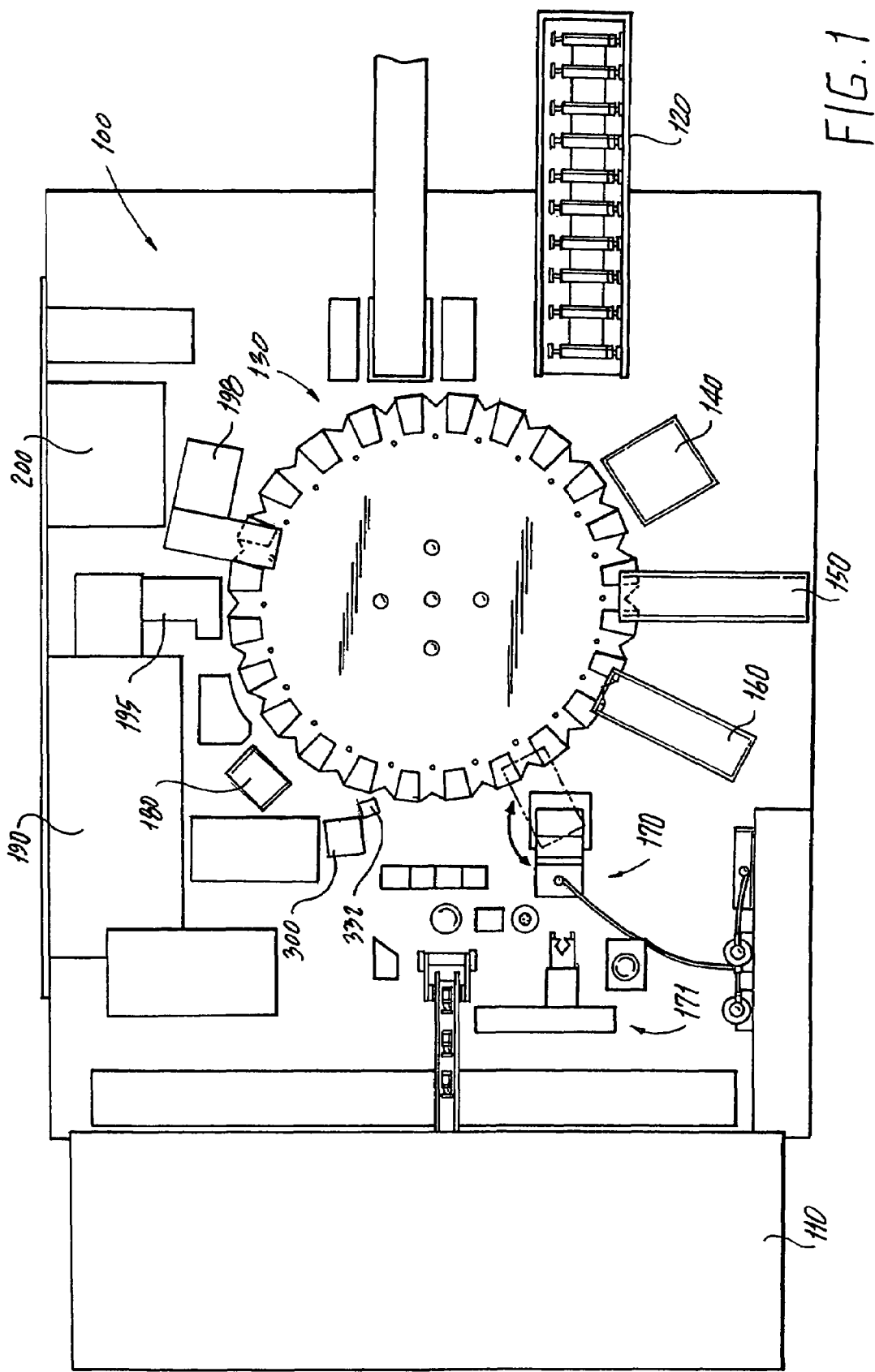
FIG. 1 is a diagrammatic plan view of an automated system for preparing a medication to be administered to a patient.

The present invention is directed towards an imaging system and a method for calculating a volume of liquid that is in a container by capturing and storing the captured image and then performing a number of operations on the captured image to yield data that is used to calculate the volume of the liquid in the container. The calculated volume can then be compared to a desired volume and if there is a difference that lies outside any tolerance value, then appropriate remedial action can be taken including removal of the container for further inspection and/or discarding. Any number of different types containers can be used to contain the liquid, including but not limited to, all types of glasswear, such as test tubes, and other receptacles, such as medical syringes, etc.

It will be understood that the present automated medication preparation disclosed herein can take any number of different forms that can equally be used with the vision system of the present invention. Thus, while a number of different applications are described herein, these applications are merely exemplary in nature and are not limiting in any way since it will be understood that other automated medication preparation systems can equally be used. In other words, one class of exemplary automated medication preparation typically involves the preparation and dispensing of drug products, whether they are in a bag, a syringe or via some other type of administration vehicle. For example, in one embodiment, the automated medication preparation is incorporated into a hood within an I.V. room and is constructed to be accessed in the course of manual preparation of an I.V. product. In another embodiment, that is described in great detail herein and set forth in the drawing figures, the automated medication preparation system involves the automated preparation of a syringe in which the desired medication is stored. Thus, it will be broadly understood that the present invention covers a vision system used in combination with an automated medication preparation system that includes the preparation and dispensing of a drug product (unit dose of medication). Therefore, it will be understood that as used herein, a drug vial is merely one exemplary type of drug container, while a syringe is one exemplary type of drug product container and neither is limiting of the present invention.

FIG. 1 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or more medications, etc., under proper storage conditions. Typically, medications and the like are stored in sealed containers, such as vials, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes a rotary apparatus 130 for advancing the fed syringes from and to various stations of the system 100. A number of the stations are arranged circumferentially around the rotary apparatus 130 so that the syringe is first loaded at the first station 120 and then rotated a predetermined distance to a next station, etc. as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap and extending a plunger of the syringe at a third station 150. At this point, the syringe is ready for use.

The system 100 also preferably includes a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110. Multiple readers can be employed in the system at various locations to confirm the accuracy of the entire process. Once the system 100 confirms that the sealed container that has been selected contains the proper medication, the container is delivered to a fourth station 160 using an automated mechanism, such a robotic gripping device as will be described in greater detail. At the fourth station 160, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a fifth station (fluid transfer station) 170 for injecting or delivering a diluent into the medication contained in the sealed container and then subsequently mixing the medication and the diluent to form the medication composition that is to be disposed into the prepared syringe. At this fluid transfer station, the prepared medication composition is withdrawn from the container (i.e., vial) and is then delivered into the syringe using a robotic transfer apparatus 171. For example, a cannula can be inserted into the sealed vial and the medication composition then aspirated into a cannula set. The cannula is then withdrawn from the vial and is then rotated relative to the rotary apparatus 130 so that it is in line with (above, below, etc.) the syringe. The unit dose of the medication composition is then delivered to the syringe, as well as additional diluent if necessary or desired. The tip cap is then placed back on the syringe at a sixth station 180. A seventh station 190 prints and station 195 applies a label to the syringe and a device, such as a reader, can be used to verify that this label is placed in a correct location and the printing thereon is readable. Also, the reader can confirm that the label properly identifies the medication composition that is contained in the syringe. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 198 located prior to the unloading station 200. The various devices that form a part of the system 100 as well as a detailed explanation of the operations that are performed at each station are described in greater detail in U.S. patent application Ser. Nos. 10/728,371; 10/426,910; 10/728,364; and 10/728,363 as well as International patent application Ser. No. PCT/US03/38581, all of which are hereby incorporated by reference in their entirety.

According to one specific embodiment where the present invention is employed in a medication preparation environment, a vision gauge system 300 is provided and illustrated in FIGS. 1-8 as being a discrete station and is designed to perform 100% inspection of a recently filled syringe 302 before the syringe 302 is advanced downstream to another station, such as a station that places the cap back onto the syringe 302 in the case of the automated medication preparation system described above. More specifically, the vision gauge system 300 and its related software perform an image capture upon request from the system software. In one arrangement, the gauge system 300 is positioned to view the syringe 302 at a station that is immediately downstream of a fluid transfer station adjacent the reconstituted container fill station. As will be described in more detail below, the image of the syringe 302 encompasses a view of the entire syringe 302 from one end 304 (cannula end) to the other end 306 (finger flange) or at least captures a view of where the fluid is contained. The vision system 300 is configured such that it incorporates a means for measuring the fluid level and thus, the fluid quantity that is contained in the syringe 302.

As will be understood, the present invention is not limited to merely being used in medication preparation applications, as described herein, but rather it has much wider applications. In other words, the present invention can be used in a number of other settings that require precise measurement of a liquid in a container.

More specifically, the means for measuring the fluid level uses a measurement technique that utilizes image processing to detect and ensure the accuracy and integrity of the fluid level within the syringe 302. An image is taken of the syringe 302 in front of a specifically designed background 310 that amplifies and enhances visually the fluid level within the syringe 302. An image is taken of the syringe in front of the background 310 with this resulting image being a bi-furcated image of the syringe, with one half of the syringe having a first contrast, while the other half of the syringe has a second contrast. As described in more detail below, one half of the background has a darker contrast then the other half of the background. The combination of the different contrast background with the vision system permits easy and precise detection of the fluid contained in the syringe 302 and more particularly, the vision system 300 greatly enhances fluid detection and accordingly, facilitates calculation of the volume of fluid within the container (syringe).

According to a first embodiment, the vision system 300 is based on a black and white color background contrast design and more particularly, the present inventors have discovered the advantageous benefits provided by constructing the background 310, such that a first half 312 has a darker contrast (e.g., a black color) and a second half 314 has a lighter contrast (e.g., a white color), and then capturing an image of the syringe 302 in front of the two-colored background 310 using a camera 330 or the like. As best shown in FIG. x, the first half 312 has a black vertical shape and the second half 314 has a white vertical shape. The syringe 302 is preferably positioned such that the rough center of the syringe 302 is disposed along the interface edge between the black half 312 and the white half 314. This results in about one half of the syringe body being placed in front of the black half 312, while the other half is in front of the white half 314 when looking directly on the syringe body.

Figure 2:
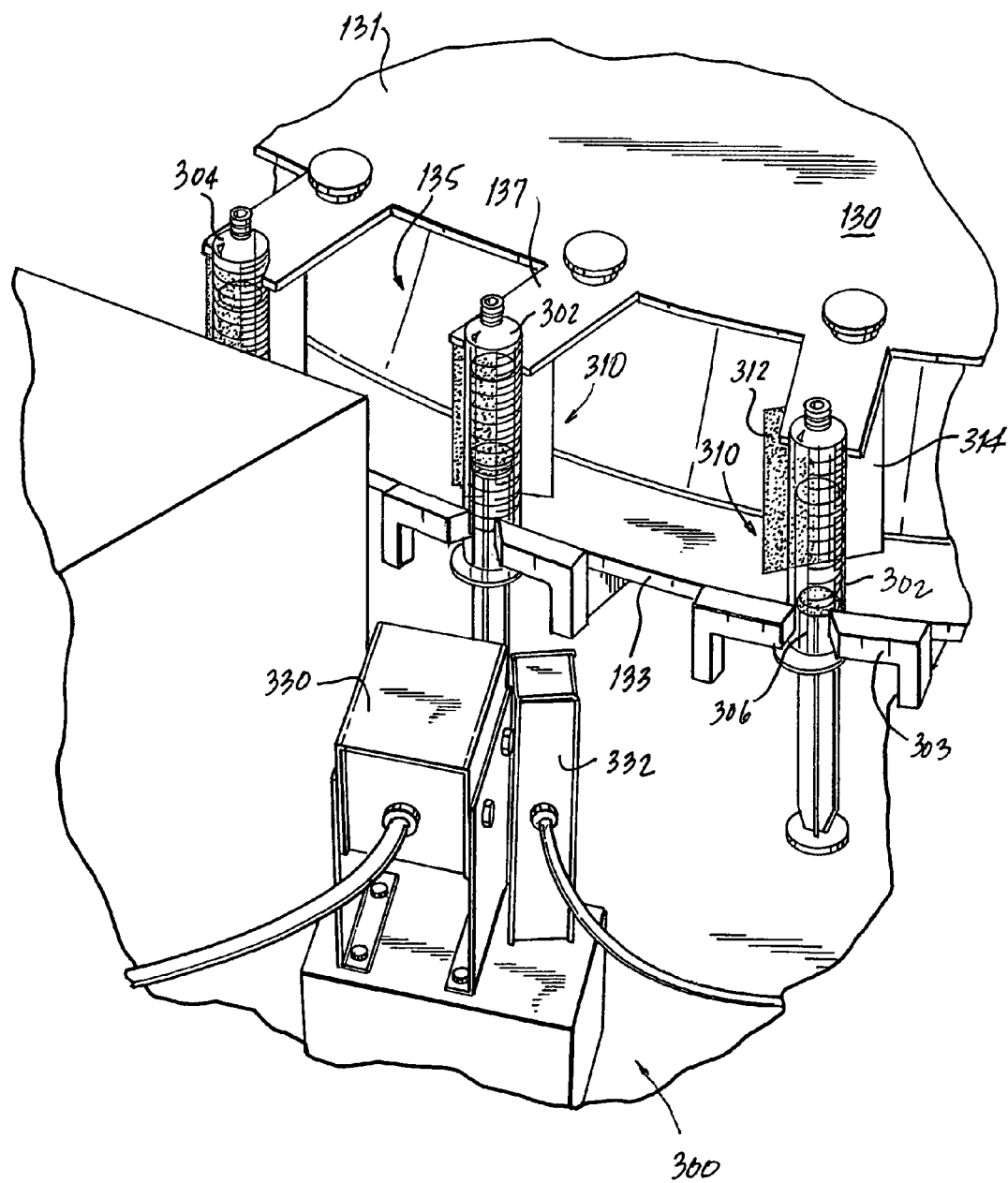
FIG. 2 is a local perspective view of a vision system according to one exemplary embodiment for measuring of a volume of liquid held in a container.
Figure 3:
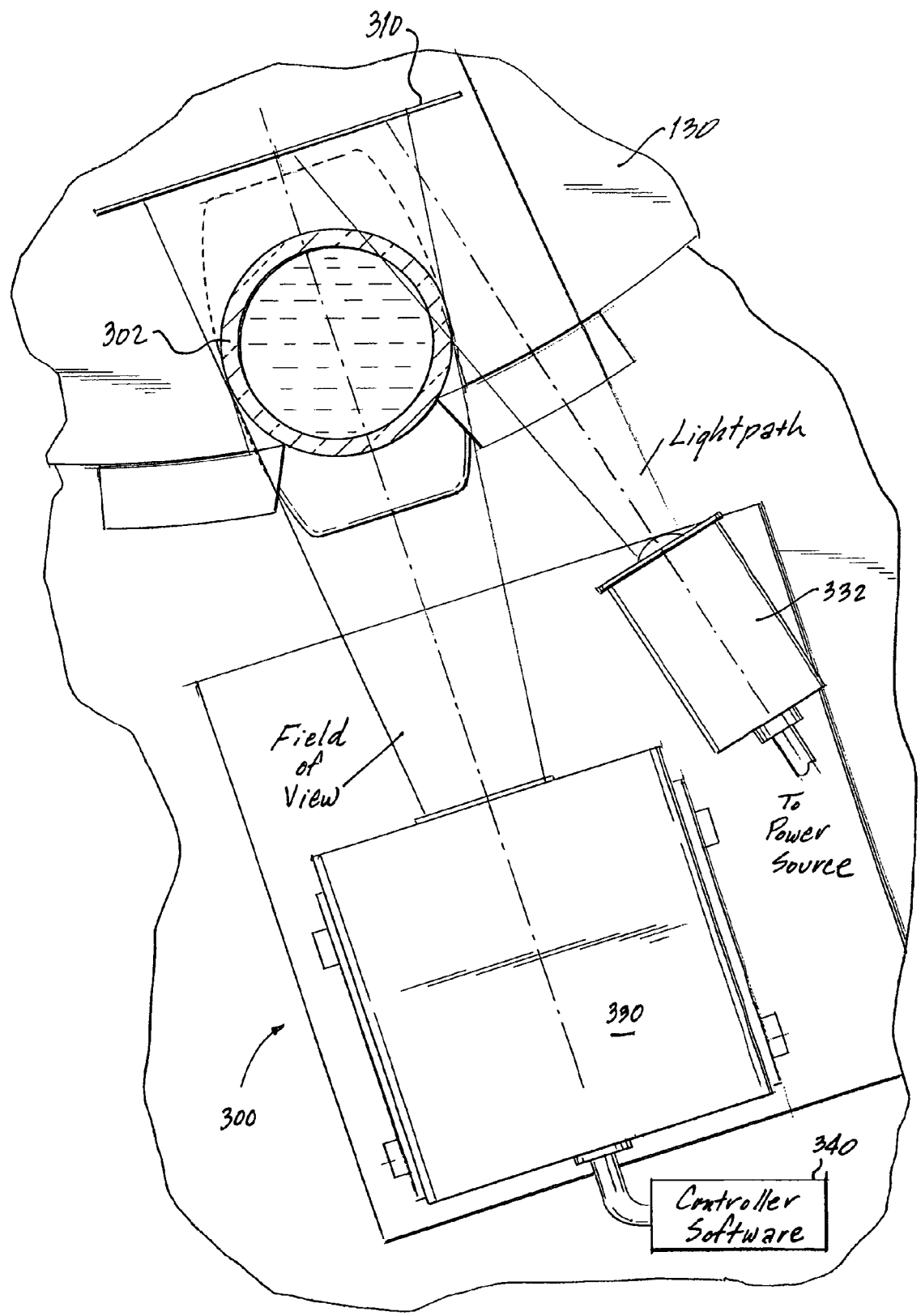
FIG. 3 is a top plan view of the vision system of FIG. 2.
Figure 4:
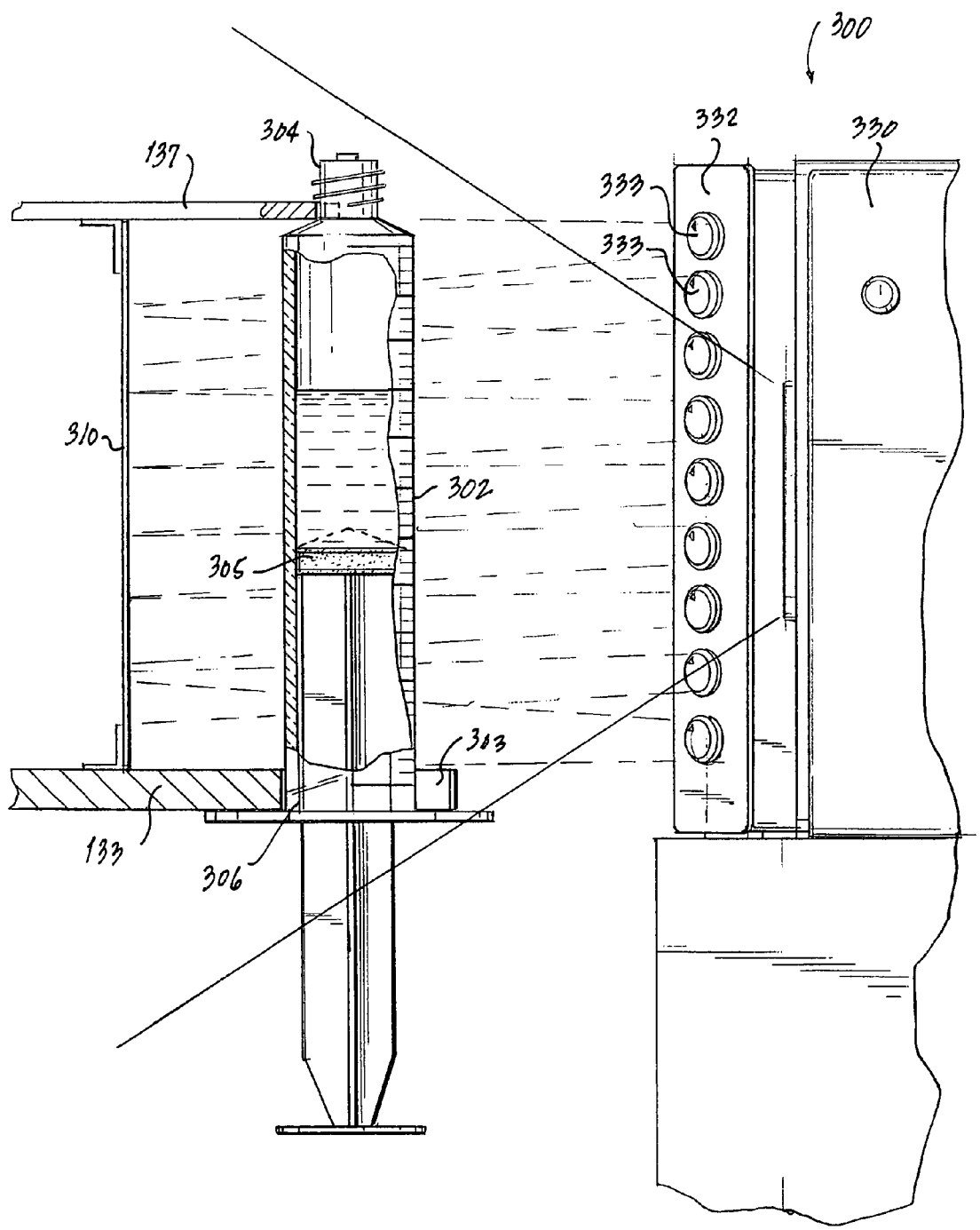
FIG. 4 is a local side elevation view, in partial cross-section, of the vision system of FIG. 2 showing a volume of liquid in a syringe.

When the syringe 302 is placed in front of the background 310, the two toned design (e.g., black and white) of the background 310 results in a two toned image being formed and captured when the syringe 302 is imaged in front of the background 310. In FIG. 2, one exemplary lay out is shown for orientating the camera 330 relative to the syringe 302 and more particularly, for orientating the camera 330 towards the rotary dial 130 on which the syringe 302 is held so that the syringe 302 is disposed between the camera 330 and the background 310.

As shown in FIG. 2, each syringe 302 is held on the peripheral edge of the rotary dial 130 by a mechanism, generally indicated at 303. The dial 130 includes an upper face member (plate) 131 and an opposing lower face member (plate) 133 with a space 135 being formed therebetween. When the syringe 302 is securely coupled to the dial 130, the upper luer (cannula) portion of the syringe 302 seats against a finger 137 that forms a part of the upper face member 131, while one end of the syringe barrel seats against the lower face member 133 by being received in a notch formed therein. The syringe barrel is thus disposed within the space 135. The spacing between fingers 137 thus corresponds generally to the spacing between syringes 302 and it is within these areas between syringes 302 that the black and white backgrounds 310 are disposed. As shown in FIG. 2, between any pair of syringes 302 and extending vertically in the space 135 between the upper face member 131 and the lower face member 133 is one black and white background 310. As mentioned, the black and white background 310 is formed of an element 312 having a black color and an adjacent element 314 having a white color. The two elements 312, 314 can be formed of any number of different materials so long as they have the requisite black and white colors; however, in one embodiment, the elements 312, 314 are formed of sturdy colored paper products.

The camera 330 is disposed at a location that is downstream from a station where the syringe is filled with a unit dose of medication (content) but the station is preferably prior to a station where a cap or the like is placed back on the syringe 302 although this is not critical. What is critical is that the camera 330 be orientated downstream of the fluid transfer station where the contents are delivered to the syringe 302 since the vision system 300 is naturally for use after the medication has been delivered to the syringe 302.

In the illustrated embodiment and according to one preferred embodiment, the camera 330 also has a complementary light source 332 that ensures that the background 310 is properly lit during the process of capturing the image of the filled syringe 302. The light source 332 directs light on the white element 314 of the background 310 that is adjacent to the syringe 302, whose image is to be captured by the camera 330. A number of different light sources 332 are suitable for use in the present invention in combination with the camera 330. The illustrated light source 332 is a tower-like device that has a plurality of light bulbs 333 that are orientated vertically along the height of the light source 332. By having a number of light bulbs 333 arranged axially along the height of the light source 332, more uniform lighting of the entire white element 314 is achieved from its bottom to its top. The light source 332 is thus designed to further enhance the color contrast between the black element 312 and the white element 314 of the background since the system 300 may be used in a setting that does not especially have the best lighting and also, the relative positions of the syringe 302 to the background 310 and also between the background 310 and the camera 330 can cause the white element 314 to be shaded too much and therefore, the light source 332 serves to illuminate the white element 314.

Figure 9:
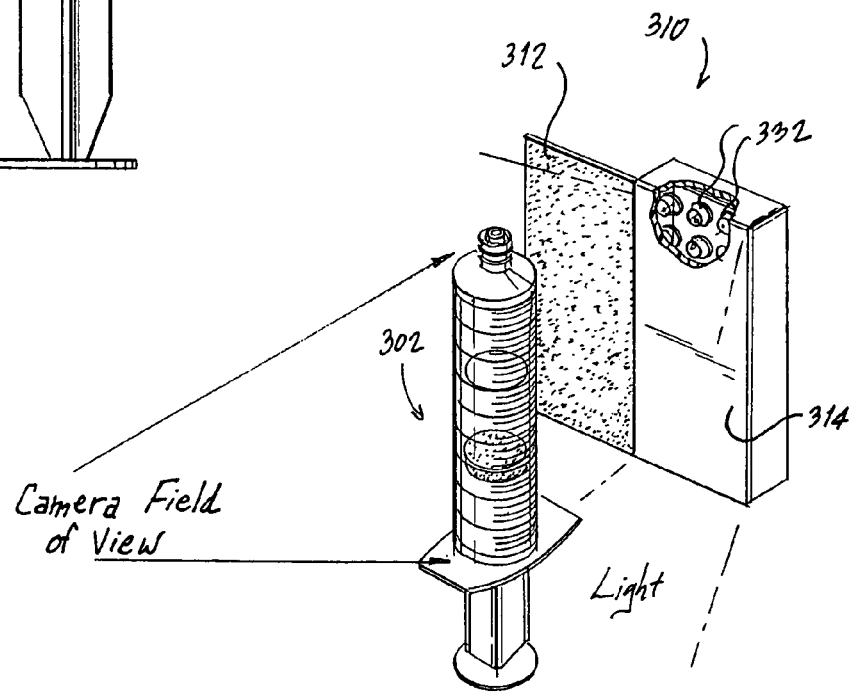
FIG. 9 is a perspective view of the syringe in front of a background according to another embodiment where one side of the background is a backlit panel.

Alternatively and as shown in FIG. 9, the light source 332 can be located behind a translucent panel that serves as the white element 314. In other words, instead of having the light source 332 in the form of an external light tower, the light source can be located behind the white element 314 of the background 310 so as to controllably illuminate the white element 314.

While in some applications, the camera 330 can be positioned directly in front of the held syringe 302 with the background 310 being formed of the pair of black and white elements 312, 314 directly behind the syringe 302 (i.e., a pair of elements 312, 314 between one pair of adjacent fingers 137), this is not a required camera orientation since the camera 330 can be orientated at an angle to the filled target syringe 302 whose image is to be captured so long as the image captures approximately one half of the syringe 302 in front of the black element 312 and the other half of the syringe 302 in front of the white element 314. In the illustrated arrangements, the black side 312 is on the left and the white side 314 is on the right; however, it will be appreciated that even this is not a requirement since the opposite is equally true in that the background 310 formed with the white side on the left and the black side on the right. What is important is that one half of the background is black or dark colored and the other half of the background is white or light colored and that one half of the syringe barrel is disposed in front of one half or the background 310 and the other half of the syringe barrel is disposed in front of the other half of the background 310.

The camera 330 and the light source 332 are preferably mounted stationary relative to the rotating dial 130 and therefore, the rotation of the dial 130 causes syringes 302 to be brought into alignment with the image field of the camera 330 so as to permit an image of the syringe 302 to be captured by the camera 330. After the image is captured, the dial 130 rotates and a new filled syringe 302 is brought into the target position and its image is captured. This process continues in a fully automated manner since all of the components at all of the stations of the present system 100 are fully integrated with one another through a master controller or the like.

Figure 5A:
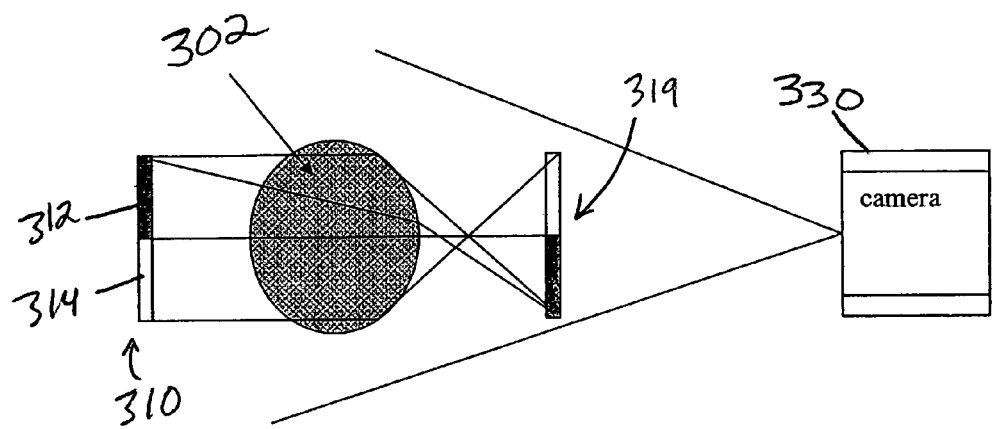
FIG. 5A is a cross-sectional view of the syringe and vision system to illustrate the optical properties of the lens formed by the syringe.

FIGS. 5-7 illustrate the present invention and shows one syringe 302 in front of the background 310 with a cylinder lens 320 defining the area in the syringe 302 where the fluid is present and the area where the fluid is absent and only air is present. It will be appreciated that the present applicants have discovered that the cylindrical lens 320 is formed due to the optical properties of the syringe 302 when it is filled with liquid. It is well understood that a simple lens bends the light coming through the lens and the optical properties of the lens material (usually glass or plastic( determines how much the light is bent. FIG. 5A generally illustrates how the syringe 302 acts as a lens with reference to the camera 330 and the background 310. In particular, a cross-section is taken through the portion of the syringe that contains a liquid and this portion of the syringe acts as a lens, in this case a cylindrical lens, that is formed by the plastic syringe and the liquid contained therein. As shown in FIG. 5A, the optical properties of the lens 320 causes a reversal of the black and white background 312, 314, as indicated in the inverted image, generally indicated at 319. In other words, there is an inversion of the image due to the optical properties of the lens 320 and this directly results in the image captured by the camera 330 appearing as shown in FIG. 6 (i.e., the image of the background being inverted at locations where the liquid is present in the syringe).

It will be appreciated and is clearly visible in FIGS. 6-7 where the liquid above a plunger 305 of the syringe 302 is located since the liquid lens 320 (formed below the meniscus) inverts the black and white background to white-black. In other words, the half of the liquid that is present in front of the first half (black side) 312 is inverted and the liquid appears to be light (white) due to the action of the cylinder lens 320, while and conversely, the liquid that is present in front of the second half 314 appears to be darker (black) due to the cylinder lens 320. However, above the cylinder lens 320, the normal black and white background shows through the syringe 302. For example, as can be seen, above the meniscus 320, the background 310 appears through the body of the syringe 302 (e.g., a translucent body) and reflects the actual color of the halves 312, 314 of the background 310 that is disposed behind the syringe 302. In other words, the image that is generated using the vision system 300 advantageously enhances the demarcation between any air that is within the syringe 302 and the liquid that is within the syringe 302. The line between the air and the fluid is enhanced dramatically in the captured image.

Any number of different types of cameras 330 are suitable for use in the present invention with one suitable camera 330 being a web camera, such as a Logitech 640×480 pixel camera. However, other digital cameras can equally be used. The camera 330 may or may not be of a digital type and therefore, if the camera 330 is initially not of a digital type, then the vision system 300 is operatively coupled to hardware including software 340 that is designed to process the captured image and digitize it into a digital image that is stored in a computer memory. The vision gauge software 340 operates on the image to extract syringe location so as to be able to determine the exact location and quantity of fluid that is contained within the syringe 302 so as to determine whether the unit dose has been correctly discharged and delivered to the syringe 302.

Figure 8:
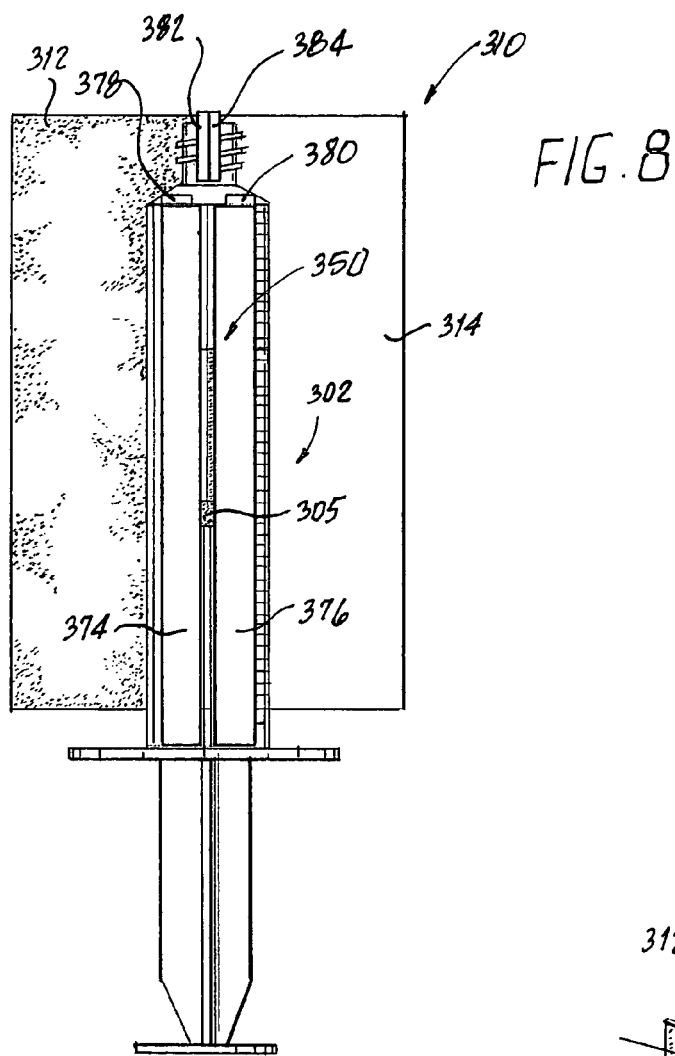
FIG. 8 is a front elevation view of the syringe in front of the background showing measurement zones superimposed on the syringe.

For example, the vision gauge software 340 can be constructed so that it divides the captured image into a predetermined number of regions, areas or zones 350 that are used in the operation to enhance the detection of the fluid level within the syringe 302 as best shown in FIG. 8. It will be appreciated that syringes 302 can come in a number of different sizes and shapes. For example, syringes 302 are typically classified by the quantity of fluid that they can carry (i.e., a 10 ml syringe, 100 ml syringe, etc.); and therefore, the exact construction of the syringe 302 is typically not only dependent upon the quantity that it can carry but also other factors, such as manufacturer's specifications, etc. Accordingly, even for syringes that can store the same amount of fluid (e.g., a maximum fill), the exact shapes and sizes of these syringes can vary. In other words, the heights and diameters of the bodies of the syringes can vary from one to another.

Thus, it is desirable for the vision gauge software 340 to be programmable and permit the user or operator to input syringe indicia information, such as a model number or product name or other manufacturer's information or indicia. By inputting this information, a controller operatively coupled to the software 340 can instruct how the vision system 300 should proceed with processing the captured image. For example, once the type of syringe 302 is known by the system 300 by reading the inputted information, the system 300 can operate on the captured image in the appropriate manner to ensure a proper detection of the fluid level. In other words, after receiving the inputted information, the software 340 can be programmed so that a database is accessed that contains a listing of the various types of syringes 302 and the respective number and dimensions of the regions 350 that are overlaid over the captured image.

In the example shown in FIG. 8, the image is digitized and the software 340 operates to divide the captured image into a black side 370 and an opposing white side 372 and more particularly, the image is divided into a first syringe body zone 374, a second syringe body zone 376, a first syringe funnel zone 378, a second syringe funnel zone 380, a first syringe cannula zone 382, a second syringe cannula zone 384. As shown in FIG. 8, the first syringe body zone 374, the first syringe funnel zone 378, and the first syringe cannula zone 382 are associated with the black side 370 and the second syringe body zone 376, the second syringe funnel zone 380, and the second syringe cannula zone 384 are associated with the white side 372. The different zones relate to different areas of the syringe, relative to a height thereof, on each of the black side 370 and the white side 372. While, one exemplary lay out includes the above mentioned six different zones, it will be appreciated that the precise number of zones is variable.

In the illustrated embodiment, each syringe body zone corresponds to the major fluid containing body of the syringe 302, each syringe funnel zone corresponds to the small area between the cannula or tip of the syringe and the syringe body, and the cannula zone corresponds to the area that is within the cannula or tip portion of the syringe through which the fluid is both discharged and received.

It will also be appreciated that since the image of the syringe 302 that is before the camera 330 in a target location is digitized and stored in memory as well as being optionally shown on a display that is associated with the vision gauge system 100, the image, and more particularly, the regions or zones thereof, can be divided into individual pixel coordinates to better identify and express certain occurrences, such as the meniscus location or the location of the plunger, etc. It will also be realized that the pixel coordinates (numbers) extend not only across a width of each zone, and thus the width of the syringe, but they also extend along the length or height of the syringe as well. Thus, it is very simple to express the location of the meniscus (the fluid/air boundary) in terms of pixel numbers that define the meniscus location in terms of its position relative to the entire length of the syringe 302. For example, if the exemplary syringe 302 has a volume of about 10 ml and this corresponds to 600 pixels in length, then any location along the length of the syringe 302 can be identified if the pixel number is known. For example and as described in greater detail later, if it is determined that an item of interest, such as the meniscus, is located at the pixel number 300, then this location corresponds to the item being located at the 5 ml mark.

After capturing the image of the syringe 302 and its contents in front of the background 310 and digitizing it and dividing it into the predetermined regions or zones, the first and second syringe body zones 374, 376 are then scanned in both the black side 370 and the opposing white side 372 to form feature vectors that can be analyzed so as to calculate the precise fluid level within the syringe, and thus, the volume of the unit dose of medication that has been delivered to the syringe 302.

Figure 10:
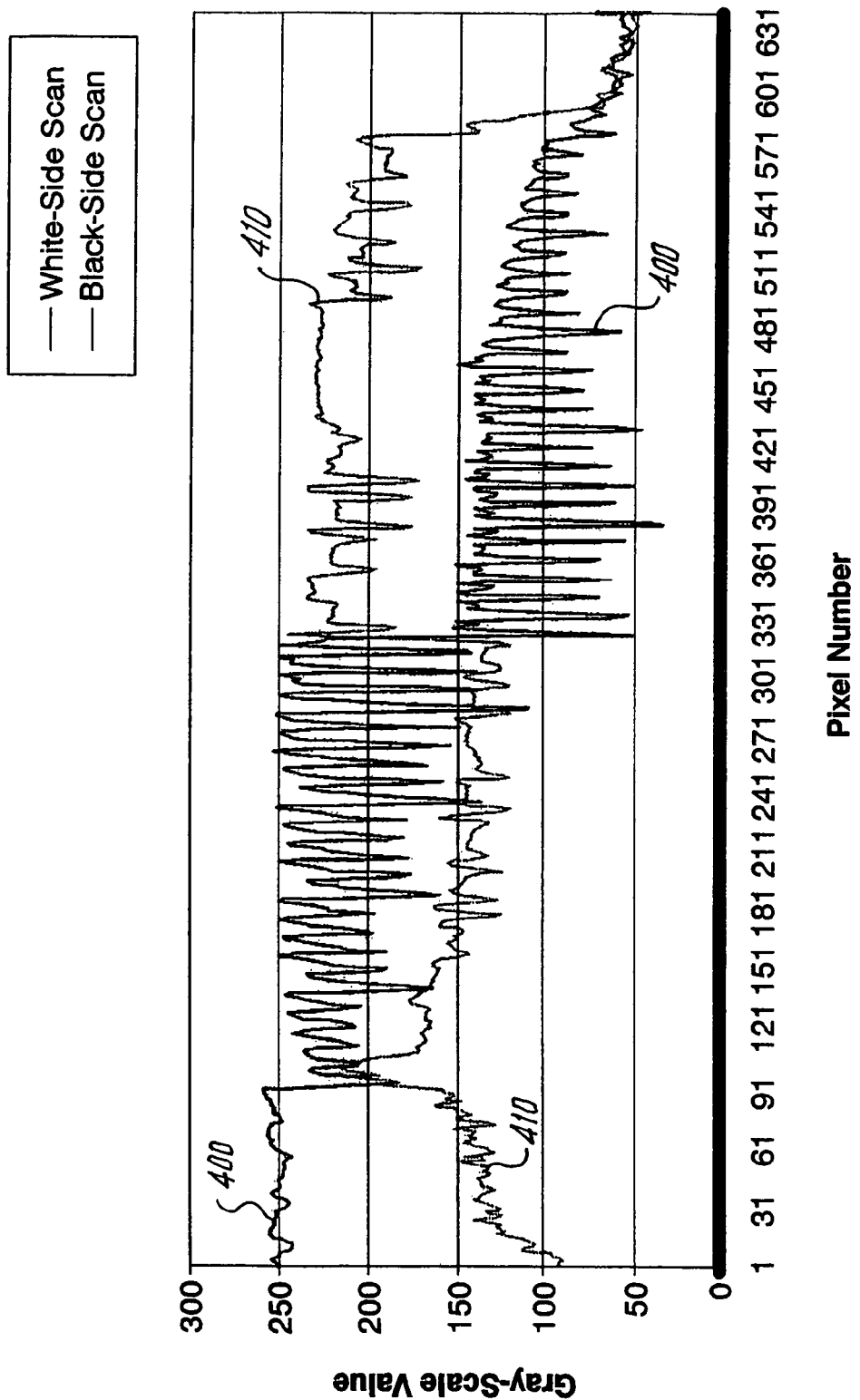
FIG. 10 is a plot shown a scan of two halves of the syringe to detect gray-scale values along a length of the syringe.

More specifically, FIG. 10 is a diagramatic plot that represents scans along a length of the syringe 302 and illustrates two exemplary feature vectors, namely, a white side scan vector 400 and a black side scan vector 410. The vectors 400, 410 are shown in a graph that has as its x-axis (vertical axis) a gray-scale value and as its y-axis (horizontal axis) a pixel number. In other words, FIG. 10 shows the scans of the two halves of the syringe 302. The high frequency lines are the result of the scale (graduations) that is typically imprinted onto the body of the syringe 302. The scanner is preferably a component of the complete software package that is designed to read specific regions or zones of the captured image in order to detect and calculate the fluid level of the unit dose within the syringe body. The scanner software application is in communication with the controller and the other computer hardware and software so that the scanner can be directed to one of the predetermined zones that each represents a specific region of the syringe 302.

In FIG. 10, the illustrated scan is one which, going from left to right, scans from the top (first end 304) of the syringe 302 to the bottom (second end 306) of the syringe 302. The differences between the vectors results because of how the black side 312 and the white side 314 of the background 310 influence how the fluid in the syringe 302 is captured in the image and more particularly, the above described inversion of the black-white background to white-black in the area where the liquid is present in the syringe 302.

Figure 11:
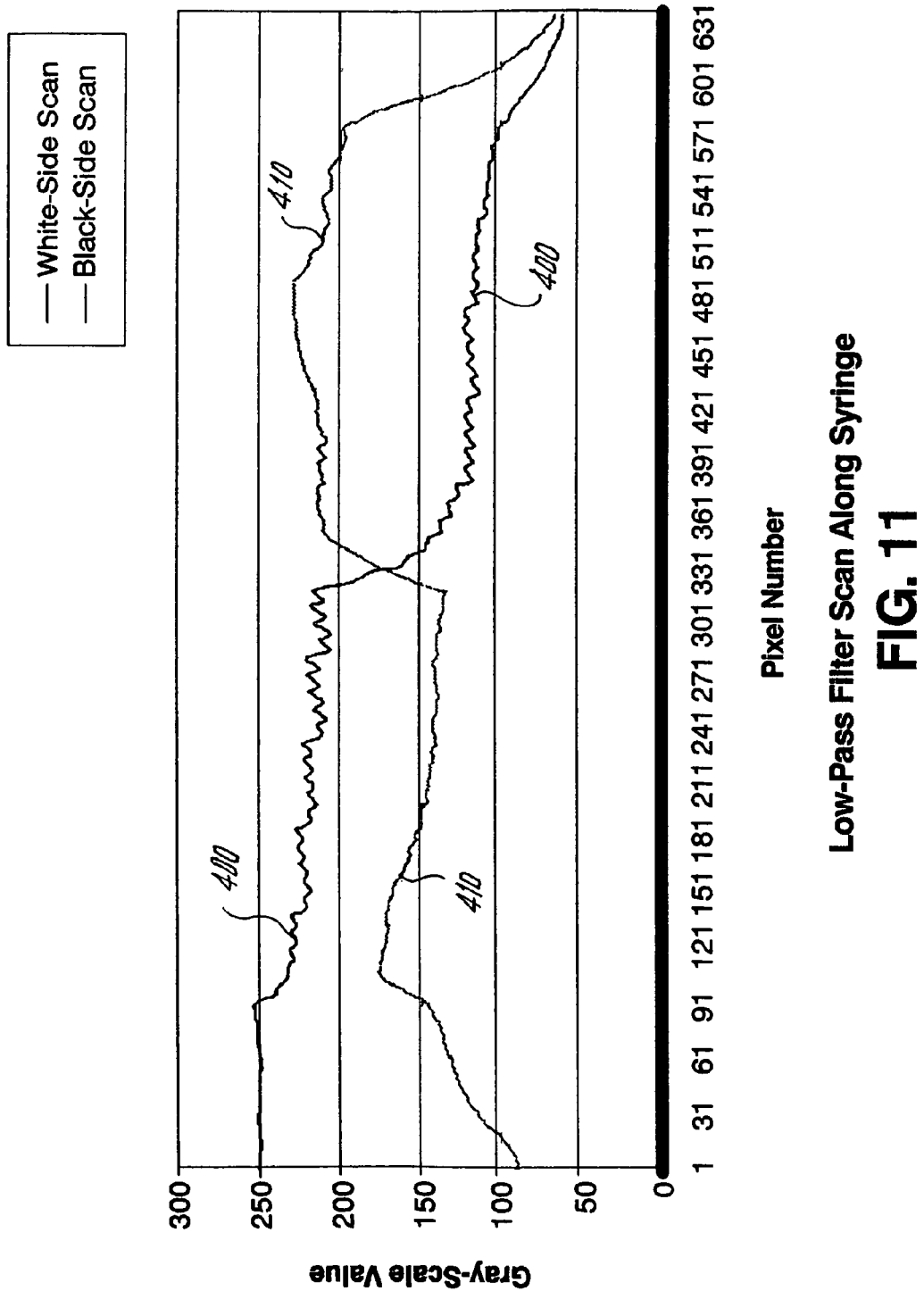
FIG. 11 is a plot showing the results of low-pass filtering of the vectors generated in the graph of FIG. 10.

The feature vectors (black side and white side vectors) 400, 410 are then low-pass filtered and the results are shown in FIG. 11. As is known, a low pass filter transmits spatial frequencies below the cutoff frequency and substantially attenuates the spatial frequencies above the cutoff frequency. The low-pass filtering of the vectors 400, 410 of FIG. 10 smoothes out the vectors and provides vectors that can be more easily operated on as the analysis of the captured image continues. The axes in FIG. 11 are the same as the axes in FIG. 10, namely a gray-scale value axis and a pixel number axis. As can be seen in FIG. 11, at the left side of the graph, the black-side vector 400 and the white-side vector 410 are separated from one another with the white-side vector 410 being on top of the black-side vector 400 and then at some point, the two vectors 400, 410 cross over one another. This point can be referred to as a cross-over point. It will be appreciated that this cross-over point represents the air-liquid interface point. After the cross-over point, the black-side vector 400 is on top of the white-side vector 410 in the FIG. 11 indicating a higher gray-scale value being detected on the black-side 400 relative to the white-side 410.

According to the first method of calculating the volume of liquid in the container, the next step in the process to enhance the detection of the fluid level in the syringe 302 is to perform an operation on the vectors 400, 410, whereby, the white-side vector 410 is divided by the black-side vector 400 to form a ratio vector 420 for the scanned area, namely the cylindrical body area of the syringe 302 that is represented by the first and second syringe body zones 374, 376 shown in FIG. 8.

Figure 12:
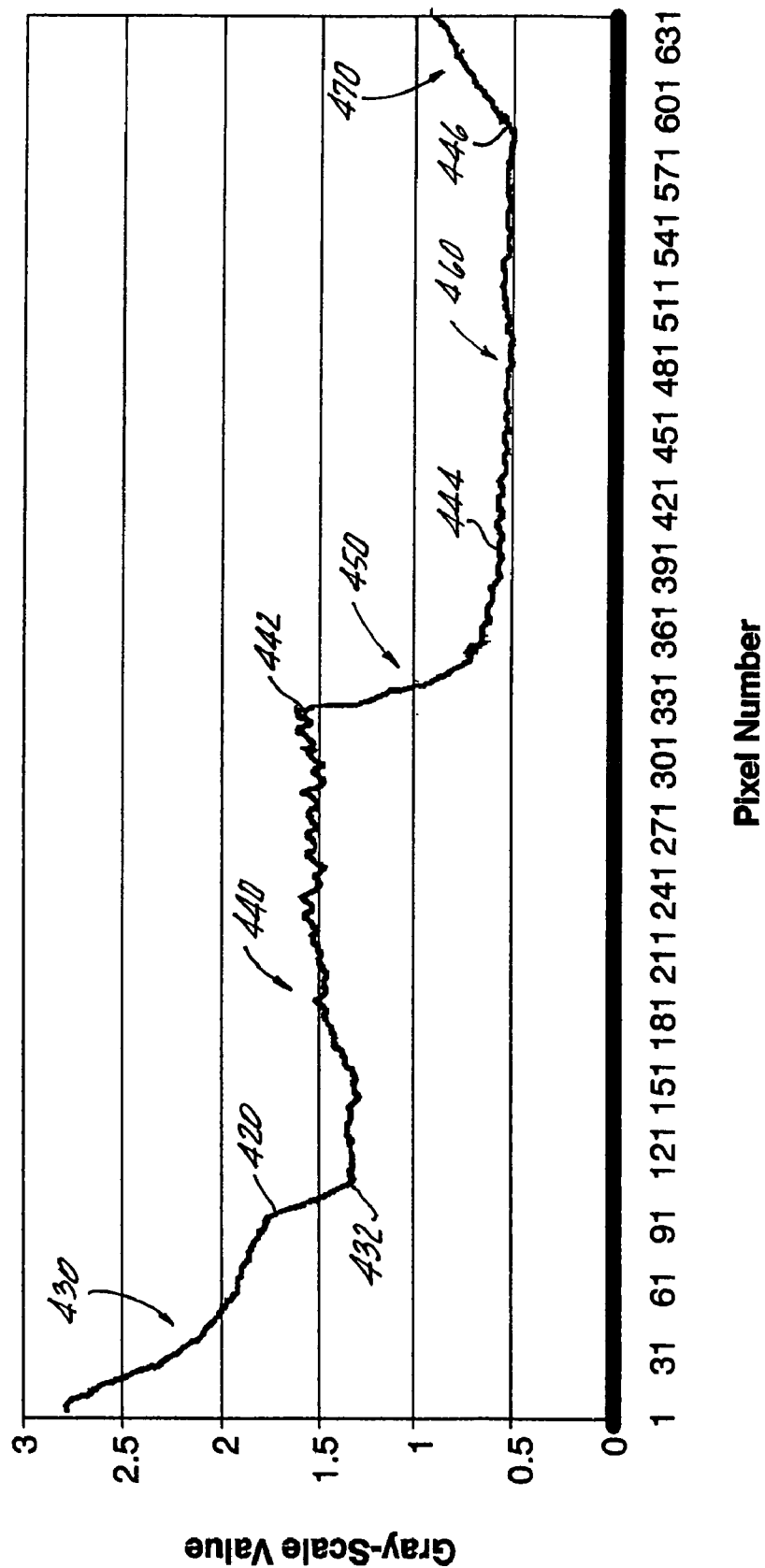
FIG. 12 is a plot of the vectors of one half of the syringe divided by the vectors of the other half of the syringe to form a ratio vector for a select area of the syringe.

A plot of the ratio of the white to black-side scans is shown in FIG. 12 as the ratio vector 420. The plot has as its x axis the ratio of white to black-side scans, while the y axis is the pixel number, which as previously indicated can be correlated to the barrel length of the syringe 302. The ratio vector 420 can generally be characterized as having three different regions, zones or segments that each describes or is indicative of different information that relates to the fluid level within the syringe 302 that is captured in the image being analyzed. More particularly, the ratio vector 420 includes, from left to right in FIG. 12, a first region or zone 430, a second region or zone 440, a third region or zone 450, and a fourth region or zone 460. By analyzing these particular regions of the ratio vector, as described below, it is possible to determine the location of the air-liquid interface and the location of the rubber plunger of the syringe 302. These two locations can then be fed into a calibration table to calculate the total volume within the syringe.

In FIG. 12, the first region 430 of the ratio vector corresponds to a transition from a top structure of the syringe into air that lies above the liquid in the syringe 302. Within the first region 430, the ratio vector has a downward slope until a point where it generally levels off at a point 432 that represents the presence of air above the fluid in the syringe 302. The air phase is thus represented by the second region 440. Within the second region 440, the value of the ratio vector only deviates over a small range over the length of the syringe barrel (as measured by pixel number) until there is a drop off of the ratio vector, as indicated at 442. This drop off is generally a noticeably sharp decline in the value of the ratio before the ratio value again levels off at a point 444 to a more linear like segment that lies within the third region 450. The third region 450 begins at the drop off 442 and continues to the point 444 where the linear segment begins. It will be appreciated that the pronounced drop off that defines the third region 450 actually demarcates the air-fluid transition zone where the meniscus of the fluid lies and this explains why the drop off 442 is sharp but it is not a 90 degree drop off due to surface characteristics of the fluid in the meniscus region.

It will therefore be recognized that the fluid region 440 begins at point 444 and continues until a point where there is a rise in the vector from the linear segment. The fourth region 460 includes the linear segment of the vector that begins at point 444 and continues to point 446 where the vector starts to steadily rise and depart from the general linear characteristics of the linear segment. The fourth region 460 represents the fluid region and therefore, the difference between the two pixel numbers associated with the fluid transition zone (air/liquid transition) and the point 446 represents the height or distance of the fluid within the syringe barrel in terms of pixel numbers. As previously mentioned, there is a direct correlation between pixel number and location along the length of the syringe with pixel numbers being capable of being correlated to metric measurements of this distance—this aspect is described below in relation to the discussion of how to calibrate the system. Thus, once the height of the fluid is determined in terms of pixel number and the calibration table is calculated, the pixel distance of the fluid can easily be converted to a metric measurement (volume). For example, 100 pixels is equal to 1 milliliter (ml) (i.e., a 10:1 ratio), then a fluid that extends over 300 pixels is equal to a fluid volume of 3 ml within the syringe 302. This is the general underpinnings of the present invention where a captured image can be used to accurately calculate the volume of fluid within the syringe 302. The fifth region 470 begins at 446 and represents the plunger within the syringe 302.

As is known, the volume of the fluid within the syringe 302 can easily be determined once the distance of fluid is determined using the above calculation and technique. The volume of fluid within any given syringe can be determined by the formula $V=[\pi d^2/s]$, wherein V is the volume of the fluid, d is the inner diameter of the syringe and s is the distance (top to bottom) of the fluid within the syringe 302. Thus, the total volume of fluid within the syringe is easily calculated with the system software and is compared with an inputted volume that represents the desired volume of the unit dose that should have been delivered to the syringe 302.

In terms of the construction of the system, it will be appreciated that the software associated with the operating systems and the computer of the system is configured to perform the above operations.

The present system thus incorporates a feature in the form of vision gauge 300 and associated software which when used in combination with the controller is able to first determine when an underfill or even an overfill condition exists where the volume of the unit dose of medication is actually less or more, respectively, than the prescribed volume of the unit dose that is to be dispensed into the product container. Both an underfill condition and an overfill condition are not acceptable since the product container must contain the precise amount of medication that it is supposed to have and therefore, an underfill condition and an overfill condition will result in the product container being rejected. By having a precise sensing mechanism and more importantly, having a system that can calculate the precise volume of medication that has been transferred to the syringe 302, some degree of remedial action can be taken if the product container does not have the correct volume of medication. For example, in the event of an underfill condition, the present system can correct the underfill condition by delivering an amount of medication to the actual volume of medication in the product container so as to compensate thereof and to make the actual volume of the medication in the product container equal to the prescribed volume of the unit dose of medication that is inputted into the controller by the user.

By refilling the product container with just enough medication until the product container holds the prescribed volume of medication, under weight rejection of the product container is avoided. It will be appreciated that the automated system disclosed herein is merely exemplary in nature and that there are a number of other types of automated medication preparation systems that can be used in combination with the vision gauge of the present invention so long as the vision gauge is capable of detecting and capturing an image of the syringe and the controller includes the necessary electronic boards to permit calculation of how much volume of fluid is occupied in the syringe. Refill or "top off" additions of the medication are performed to ensure that the product container holds the precise amount of medication.

In the case when the first and second syringe body zones 374, 376 are completely occupied with fluid (medication) and the medication extends into at least the first and second syringe funnel zones 378, 380 and/or the first and second syringe cannula zones 382, 384, the vision gauge 300 is configured to analyze these zones in order to determine the level of fluid within the syringe 302. When the fluid is in the funnel zones, these two sample areas will be summed and a ratio between the black and white vectors in these areas will be calculated in the manner previously described with reference to calculating the ratio in the first and second syringe body zones 374, 376. If fluid is within the first and second cannula zones 382, 384, then two small scans will be used as in the first and second body zones 374, 376 of the syringe 302.

It will also be appreciated that for every fill (of a unit dose of medication), the system 100 can be configured such that the plunger of the syringe is withdrawn an additional predetermined amount. For example and based on a number of parameters, including user input and specific consumer's specifications, the plunger can be withdrawn approximately 0.3 to 0.5 ml (after the fill in bag fill) more than is needed to draw the unit dose of medication into the syringe barrel. A nurse or the like can purge the air as they normally do before usage. If every fill is targeted to result in liquid level around 0.5 ml, for example, then the extra variation that is realized by analyzing the funnel and cannula regions would not be present. Instead and like the normal application described above, the total fluid volume is between the air-liquid interface and the plunger. The total volume is then reported back to the system software which then makes a comparison as to whether it is acceptable or not as mentioned above.

The operation of the present invention is described in more detail below with reference to FIGS. 2-12 and more particularly with reference to FIG. 12, which illustrates the ratio of white to black side scans. It will be appreciated that it is more helpful to operate on the vector that is shown in FIG. 12 since the plotting of the ratio vector normalizes out the overall image intensity and accounts for shading variations. In other words, the determination and calculation of the ratio vector offsets different light conditions (light intensity).

It will be appreciated that the control system, including the software and applications, can be configured such that the system does not locate and begin to process a signal (ratio vector) until a prescribed point or event is achieved, such as when a threshold is reached. The threshold can be a particular pixel number for a particular camera 330. For example, since the main focus of the system 300 is to determine and calculate the volume of fluid within the syringe 302, the system can be constructed so that it does not begin scanning and looking for the resulting ratio vector until a prescribed pixel point (number). In other words and according to one embodiment, the system begins the scanning and calculation operations at approximately 91 pixels which represents a beginning threshold for the particular camera that is in use. The beginning threshold can vary based upon what particular camera 330 is being used, as well as based upon the mounting and lens particulars for the camera 330.

The first step in the operating procedure is to locate the syringe; however, due to the fixed mechanical nature of the syringe mounting and its precision, it is not necessary to locate the syringe every time a new syringe is inspected. A calibration of the system, as described later, provides the information necessary to take the proper measurements. It is also possible to include reference windows in the system 300 and more particularly, the system 300 can include reference white and back windows in the form of small windows on both the black background element 312 and the white background element 314 are measured and the standard deviation of the pixels within the windows are measured. Both of these calculations are reported to the system 300. This data is useful to judge the day to day performance of both the camera 330 and the lighting 332. The right-side scan and the left-side scan are performed as previously described and the ratio of the scans is used to detect the air/liquid interface.

To detect the air/liquid interface, the ratio vector is tested against thresholds. For example and according to one method of calculating the interface, the interface is an average of two thresholds, namely a threshold (A) and a threshold (B). The threshold (A) represents the ratio value of the linear segment of the second region 440, especially as the linear segment approaches the point 442, which in FIG. 12, is about 1.5. The threshold (B) represents the ratio value of the linear segment of the fourth region 460, which in FIG. 12, is about 0.5. These two thresholds (A) and (B) represent the ratio between the vectors immediately before and after the steep drop that defines the third region and represents the transition between the air and fluid. The average between these two thresholds is thus about 1.0, which represents and is classified as being the air/fluid interface. Once the interface ratio value (1.0) is determined along the x-axis, the corresponding pixel number can be determined along the y-axis (in FIG. 12, the corresponding pixel number is about 331). The liquid/air interface is generally shown in FIG. 13 at the legend A.

After calculating the air/fluid interface, further analysis of the ratio vector is performed in order to locate and calculate the plunger position since the plunger position is needed to determine the location of the bottom of the liquid. One method for calculating the position of the plunger is to find the backside of the plunger using a scan, such as a low-pass filtered scan, e.g., FIG. 11 shows that both the white-side scan and the black-side scan in a left-to-right scan mode. In other words, using the plot of FIG. 12, the plunger is calculated in pixel space. Generally, the left-side scan is analyzed for the darkest location in the scan (i.e., the highest gray-scale value). This location is the approximate location of the plunger. The gray-scale value is recorded for this location. Then the scan is analyzed from this darkest position further down the syringe at programmable distance from the darkest position and the whitest white is recorded for this scan. The difference from the gray-scale value of the whitest white to the darkest black is used to calculate a threshold. Then from the end of the white scan backwards to the plunger darkest position, the scan is compared to a threshold derived from the difference measurement and when the threshold is met or exceeded, the lowest portion of the syringe plunger has been found. The programmable distance is variable and in one embodiment, scanning is performed which is two times (2x) the width of the plunger, e.g., a scan of between about 150-200 pixels.

Figure 13:
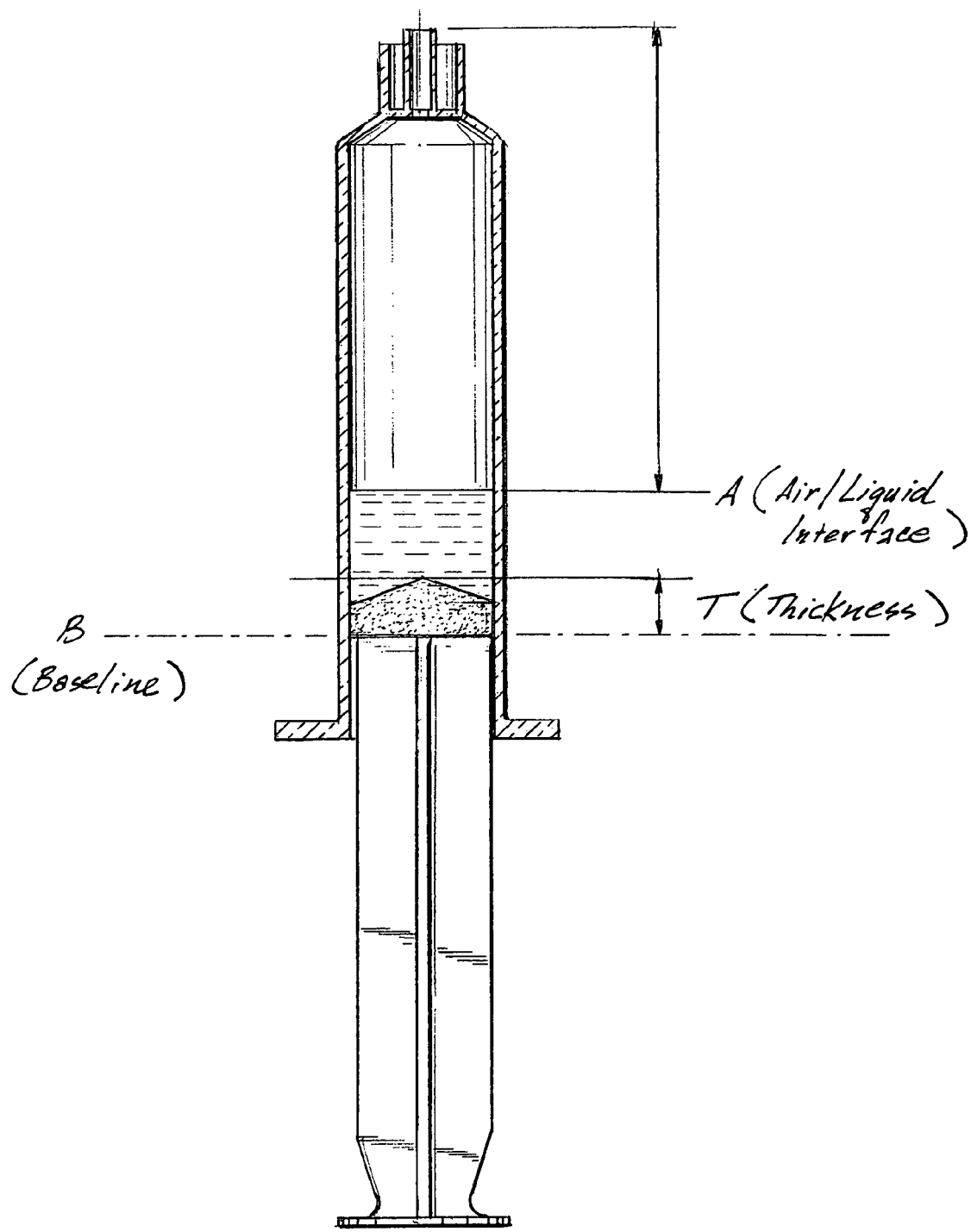
FIG. 13 is a cross-sectional view of a measurement area of the syringe illustrating various measurement points.

An understanding of this calculation and offsetting technique can be understood by viewing FIGS. 12 and 13. For example and according to one embodiment, the darkest position is 50 gray-scale value and then the scan climbs to 150 on the white-side scan. The difference between these two pixel values is 100 pixels and this represents one of the thresholds. This value (100 pixels) is then divided by 2(i.e., the value is halfed to obtain a value of 50 pixels) and is added to the darkest position value (i.e., 50+50 pixels) to obtain a value of 100 pixels which corresponds to the back edge or backside of the plunger. In FIG. 13, the backside of the plunger 305 is generally indicated by legend B.

Both the liquid level and the plunger position are sent to a conversion calculation that converts the pixel positions to milliliter (ml). Then the plunger ml value is corrected by subtracting an offset that corresponds to the actual thickness of the plunger in ml units. The offset will vary from plunger to plunger since the plungers come in a number of different thicknesses and therefore, the offset will be greater for thicker plungers. The thickness of the plunger 305 is indicated in FIG. 13 as being the distance between the legends B and C. The effect of this entire operation is then once the backside of the plunger is detected and calculated by interpreting the scan, the known offset value is used to eliminate the plunger contribution to the scanned liquid operation. The difference between the plunger position and the liquid level, then gives the amount of liquid within the syringe. In FIG. 13, the distance or amount of liquid in the syringe 302 is generally indicated by the distance between the legends A and C.

Figure 14:
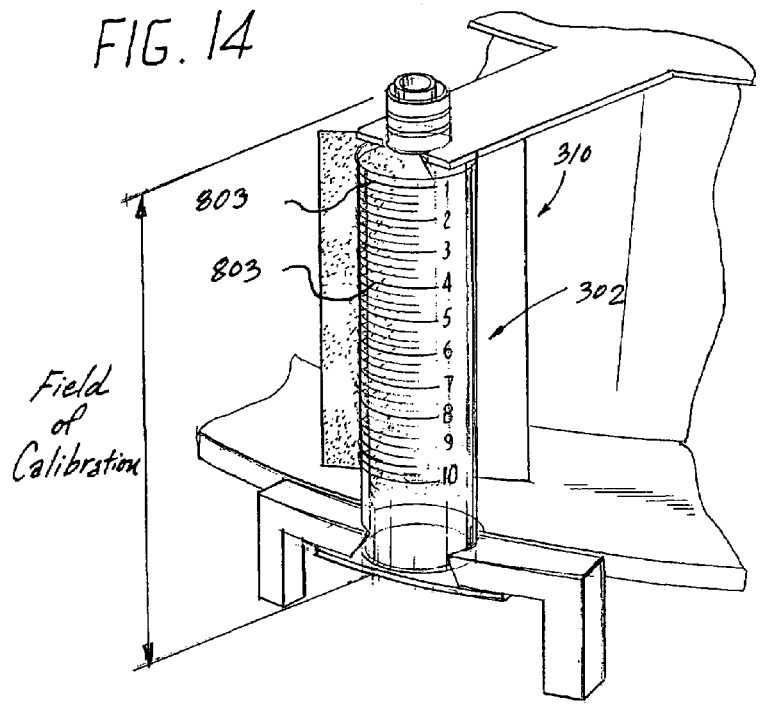
FIG. 14 is a front perspective view of an empty syringe in front of a background for calibrating the vision system.
Figure 15:
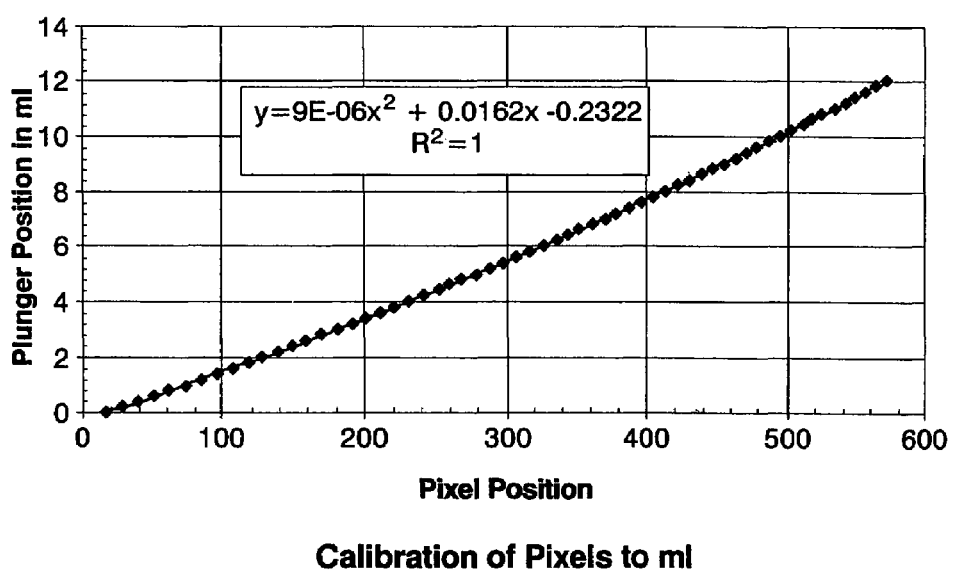
FIG. 15 is a graph showing the results of the calibration of pixels to volumetric units (ml)

Calibration of the syringe 302 is performed in the following manner. An empty syringe 302 with the plunger removed is inserted manually onto the dial. An image is taken by the camera 330 (FIG. 2) as shown in FIG. 14. As will be appreciated, the barrel of the syringe 302 contains markings or graduations 803 that are formed along the length or height of the barrel to generally indicate the volume of the liquid that is contained within the syringe 302. The calibration is performed by determining and recording the pixel locations of the 1, 2, 3 . . . 12 ml lines (graduations 803) on the syringe 302. This is determined by manipulating and operating on the digital image captured by the camera 330. The data is fit to a $2^{nd}$ degree polynomial and the coefficients are determined, as shown in Table 1, and the resulting plot is illustrated in FIG. 15. The vertical x-axis represents the ml markings 803 formed along the syringe 302, while the horizontal y-axis represents a pixel position in the captured image. The Table 1 thus provides an effective means for calibrating the pixels of the captured image to ml. For example, if the liquid is determined to be present between pixel position 100 and pixel position 500, by consulting the plot of FIG. 15, one can calculate that pixel position 100 corresponds to about the 1.8 ml marking and the pixel position 500 corresponds to about the 10 ml marking. The difference between the two, namely, 8.2 ml, represents the total volume of the liquid within the syringe 302. As previously mentioned this calibration technique and the conversion calculation are used to convert both the liquid level and the plunger position to volumetric measurement units (ml) by converting the pixel positions to milliliters. It will be understood that this calibration data and the plot of FIG. 15 is merely exemplary in nature and not limiting of the present invention. Thus, other different syringes 302 will have different calibration data and plots.

It will also be appreciated that two additional small boxes (windows) can be formed in the funnel area of the syringe and their average gray values are divided and compared to a threshold to determine if any liquid is present in the funnel area of the syringe.

Moreover, the above described method of the present invention is particularly provides excellent results when the liquid in the syringe 302 is substantially transparent (clear) in nature. As the liquid becomes more and more opaque, there is a greater chance that an error may be introduced into the calculation since the above described algorithm takes the ratio of the right side to the left side of the syringe 302 and as the left side becomes darker, there is a greater likelihood that the signal can creep inward to give less volume.

Figure 16:
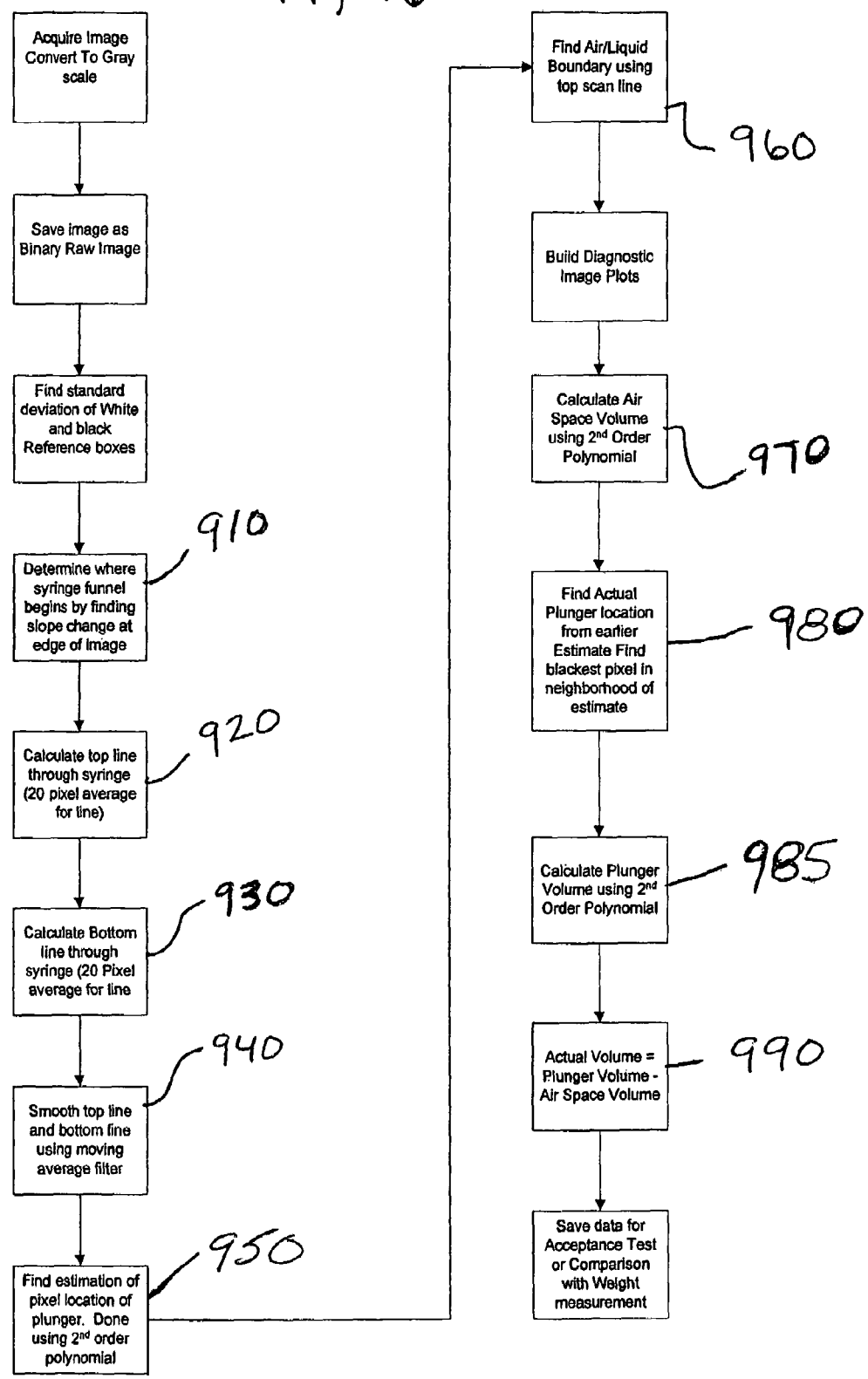
FIG. 16 is a schematic flow chart that illustrates the steps of an alternative method to determine the volume of a liquid in the syringe.

FIG. 16 is a flow chart of a method of determining the volume of liquid in a container according to a different embodiment compared to the embodiment shown in FIGS. 1-15, with this second method being particularly designed to overcome the above deficiency of the first method. This second method includes a number of steps that are the same as those steps in the previously described first method and therefore, only the differences between the two methods are highlighted and discussed in greater detail.

In step 910, a determination of where the syringe funnel begins is made by finding the slope change at the edge of the image (e.g., finds the edge of the dial in the syringe image as a calibration point). More specifically, the scan of FIG. 11 or FIG. 12 is consulted and the slope of one scan line is evaluated in a particular region. When finding the syringe funnel, the left of the scan is evaluated since the scan is a top to bottom scan and the funnel is formed at the top of the syringe. In other words, a determination of where the syringe funnel begins is determined by evaluating a change in slope of the scan line relative to the pixel number. Once the change in slope exceeds a predetermined threshold (e.g., a 50% change in slope), a point is recorded for the beginning of the syringe funnel in terms of pixel number. The calibration technique described in reference to FIG. 15 is used to calibrate this pixel number to a volumetric unit (e.g., a corresponding ml marking on the syringe body). In step 920, the top line refers to the white-side scan 400 and in step 930, the bottom line refers to the bottom side scan 410. Step 940 refers to the low pass filtering illustrated in FIG. 11. Step 950 refers to determining an estimation of the pixel location of the plunger using a $2^{nd}$ order polynomial. This step generally takes a fill estimate and iterates the volume equation until it determines the pixel position or the plunger. Since the plunger is initially pulled a predetermined distance based on the projected, intended fill volume, the determination of generally where the plunger is located can be done using the $2^{nd}$ order polynomial.

The principle difference between this second method and the previously described first method of determining the actual volume of the liquid in the syringe is highlighted in step 960. In step 960, the air/liquid interface is determined not by observing where the white-side and black-side scans cross one another, but instead, the air/liquid interface is determined by observing a change in the top scan line (white-side scan). More specifically, a preselected slope change in intensity of the top scan line is looked for since this is indicative of the air to liquid interface. For example, the slope of the top scan line is evaluated and as soon as the slope change in intensity exceeds a predetermined threshold, the point (pixel number) is recorded as being the air to liquid interface. In one exemplary embodiment, the predetermined threshold is one where the slope change is equal to or greater than a 50% change in slope intensity. Once again, the calibration technique described in reference to FIG. 15 is used to calibrate this pixel number to a volumetric unit (e.g., a corresponding ml marking on the syringe body). In this manner, the air to liquid interface is determined in the form of a volume measurement (e.g., a ml graduation on the syringe).

In step 970, the air space volume is calculated using a $2^{nd}$ order polynomial. In particular, the calibration polynomial set forth in FIG. 15 is used to convert pixels to air volume. In step 980, the actual plunger locations is found from the earlier estimate calculation. In this step, the blackest pixel is found in the neighborhood of the estimate. This step is essentially the same as previously described and more particularly, this step finds the bottom of the plunger which is the blackest pixel along the bottom line scan. This scan is done from the bottom of the syringe upward. In other words, this determines the boundary of the rear section of the plunger.

In step 985, the plunger volume is calculated using a $2^{nd}$ order polynomial. This step uses the calibration polynomial set forth in FIG. 15 to convert pixels to plunger volume. As previously described with reference to the first embodiment, this step 980 is one in which a thickness of the plunger is calculated.

In step 990, the actual volume of the liquid within the syringe is determined, with the actual volume equal to the plunger volume minus the air space volume.

The present inventors have discovered that the method of the first embodiment is particularly suited for clear liquids, while, the method of the second embodiment is particularly suited for colored liquids.

It will also be appreciated that in applications where the liquid is merely contained within standard glasswear or the like, it is not necessary to calculate the plunger position since no plunger exists. This is a much easier task since the bottom of the glasswear can be zeroed in the calibration process using the pixel position conversion technique and then the interface between air/liquid is calculated as described above by analyzing the vector ratio scan. Once the pixel number for the air/liquid interface is determined, it can be converted to an ml reading, which then yields the total volume of liquid since the bottom of the glasswear is treated as being the 0 ml position.

The present invention thus provides an efficient, alternative system and method for precisely calculating a volume of liquid in the container that overcomes the disadvantages of the prior art devices. Importantly, the present system can be easily incorporated into an automated system, such as one where a number of liquid-containing product containers are produced by an automated process, so as to provide a vision detection system that can precisely calculate whether each product container has the correct volume of liquid.

What is claimed is:

1. As system for calculating a volume of liquid that is disposed within a container comprising:
    an imaging device in the form of a digital camera that captures and stores an image of at least the volume of liquid in the container;
    a background disposed behind the container so that at least the volume of liquid in the container is disposed in front of the background,
        wherein the container is disposed between the digital camera and the background, the stored image being defined by a set of vertical pixel numbers and a set of horizontal pixel numbers, and
        wherein the background is defined by a first region that has a first color contrast and a second region that has a second color contrast; and
    a processor that performs at least on operation on the stored image including analyzing a portion of the background that is visible through the volume of liquid and appears altered relative to adjacent portions of the stored image to calculate the volume of the liquid within the container.

2. The system of claim 1, wherein the liquid is a unit dose of medication and the container is a syringe including a plunger slidably received within a barrel of the syringe.

3. The system of claim 2, wherein the barrel includes graduations formed along a length of the barrel for indicating the volume of the liquid.

4. The system of claim 1, wherein the first region is one half the entrire area of the background, while the second region is the other half of the entire area of the background.

5. The system of claim 1, wherein the first color contrast is darker than the second color contrast.

6. The system of claim 1, wherein the first region has a black color and the second region has a white color and the first region is in the form of a first vertical stripe and the second region is in the form of a second vertical stripe that is adjacent the first vertical stripe so that a vertical interface is formed between the first and second vertical stripes.

7. The system of claim 1, wherein the processor is configured to divide the image into a black-side and an adjacent white-side and dispose a graphic overlay on the stored image with the overlay dividing the image into a plurality of measurement areas, where each measurement area disposed in the black-side has a complementary measurement area disposed in the white-side.

8. The system of claim 7, wherein the plurality of measurement areas comprise a first syringe body zone, a first funnel zone and a first cannula zone all located on the black-side as well as a second syringe body zone, a second funnel zone and a second cannula zone all located on the opposing white-side.

9. The system of claim 7, wherein the processor is configured to perform a scan of any complementary measurement areas found in the black and white-sides, the scan measuring a gray-scale value of a medium detected along a length of the container.

10. The system of claim 9, wherein the processor is configured to plot feature vectors of the white-side scan and the black-side scan and then low-pass filters the feature vectors to form a low-pass filter scan, wherein the low-pass filtered feature vectors of the black-side and the white-side intersect one another at a point that represents an air-liquid interface of the liquid in the container.

11. The system of claim 10, wherein the processor is configured to calculate the white-side low-pass filtered vector divided by the black-side low-pass filtered vector in the form a ratio vector that can be plotted on a plot having ascending gray-scale values along an x-axis and ascending pixel numbers along a y-axis, wherein a point at which the ratio vector crosses 1 as measured on the x-axis represents the air-liquid interface for the liquid, whereby a liquid level representing the pixel numbers of boundaries of the volume of liquid is calculated.

12. The system of claim 10, wherein the processor is configured to locate and calculate a position of a plunger that is associated with the container by detecting a backside of the plunger and correcting the plunger position by subtracting an offset that corresponds to an actual thickness of the plunger, whereby the volume of the liquid in the container is calculated as being the difference between the plunger position and the liquid level in the container.

13. The system of claim 1, further including a calibration feature that processes an image of an empty container that includes a plurality of graduations that indicate the volume in the container so as to determine and record pixel locations for the graduations, thereby permitting pixel data to be converted to volumetric data.

14. The system of claim 1, further including: a light source that directs light on at least a section of the background.

15. The system of claim 14, wherein the light source comprises a light tower having a plurality of lights that extend along a height of the light tower, wherein the light tower emits light that is directed at a white colored half of the background, with the other half of the background having a black color.

16. The system of claim 14, wherein the light source comprises a light that is provided behind a substantially translucent panel that forms a part of the background so as to define a bright colored panel when actuated.

17. The system of claim 1, wherein the system is incorporated into an automated medication preparation system including preparation and dispensing of medication to the container, the preparation system includes an automated device for preparing and dispensing a prescribed unit dose of medication, wherein the imaging device is located downstream of the automated device.

18. The system of claim 17, wherein the automated device comprises an automated syringe preparation that includes reconstitution of the medication and delivery of the unit dose of the reconstituted medication to a syringe from a drug vial, the automated device includes a fluid delivery device for delivering the prescribed unit dose of medication to the syringe in a just-in-time for use manner, wherein the fluid delivery device is adapted to aspirate the reconstituted medication into a main fluid conduit and later discharging reconstituted medication from the drug vial into the syringe.

19. The system of claim 1, wherein the liquid is substantially clear.

20. A method for calculating a volume of liquid that is disposed within a container comprising the steps of:
provideng a background in front of which the container is placed so that at least the volume of liquid is disposed in front of the background;
operating an imaging device to capture and store an image of at least the volume of the liquid,
wherein the imaging device is digital camera and the stored image is a digital and the background is defined by a first region that has a first color contrast and second region that has a second color contrast, the first color contrast being substantially darker than the second color contrast; and
performing at least on operation on the stored image including analyzing a portion of the background that is visible through the volume of liquid and appear altered relative to adjacent portions of the stored image to calculate the volume of the liquid contained within the container.

21. The method of claim 20, wherein the first region comprises a black-colored region and the second region comprises an adjacent white-colored region; and the step of capturing the image comprises the step of illuminating the white-colored region with a light source.

22. The method of claim 21, wherein the step of illuminating the white-colored region comprises the steps of: providing a light tower that represents the light source; and emitting light from the light tower onto the white-colored region of the background; wherein the light tower is located either behind the white-colored region to provide backlighting of the white-colored region or in front of the background with the container being located between the light tower and the background.

23. The method of claim 20, wherein the step of performing at least one operation on the stored image comprises the steps of: dividing the stored image into a black-side and a white-side that correspond to black and white-sides, respectively, of the background; disposing a graphic overlay on the stored image, the graphic overlay dividing the image into a plurality of measurement areas, where each measurement area disposed in the black-side has a complementary measurement area disposed in the white-side; and scanning complementary measurement areas found in the black and white-sides of the stored image, the scan measuring a gray-scale value of scanned medium detected along a length of the container.

24. The method of claim 23, wherein the container is a syringe and the step of dividing the image into measurement areas comprises the steps of: dividing a barrel of the syringe into first and second syringe body zones formed respectively on the black-side and the white-side; dividing a funnel section of the syringe into first and second syringe funnel zones formed respectively on the black-side and the white-side; and dividing a cannula section of the syringe into first and second cannula zones formed respectively on the black-side and the white-side.

25. The method of claim 24, wherein the step of performing at least one operation on the stored image comprises the steps of: plotting feature vectors of the white-side scan and the black-side scan, the plot having ascending gray-scale values along an x-axis and ascending pixel numbers along a y-axis that measures from a top to a bottom of the captured image; low-pass filtering the feature vectors of the white and black-side scans to form a low-pass filtered scan; and analyzing the low-pass filtered scan for a point where the low-pass filtered vectors of the black-side and the white-side intersect one another, the point representing an air-liquid interface of the fluid in the container.

26. The method of claim 25, wherein the step of performing at least one operation on the stored image comprises the steps of: dividing the white-side low-pass filtered vector by the black-side low-pass filtered vector to form a ratio vector; plotting the ratio vector that includes ascending gray-scale values along an x-axis thereof and ascending pixel numbers along a y-axis thereof; and analyzing the ratio vector plot for a point at which the ratio vector crosses 1 as measured on the x-axis represents the air-liquid interface for the liquid in the container.

27. The method of claim 26, further including the step of: determining a first pixel number of the air-liquid interface of the fluid in the container; determining a second pixel number that can be used to calculate the volume of the liquid in the container; converting the first and second pixel numbers to volumetric measurement units; and calculating the volume of the liquid in the container by performing an operation on the volumetric measurement units.

28. The method of claim 24, wherein the step of performing at least one operation comprises the steps of: dividing the stored image into a black-side and a white-side that correspond to the black and white-sides, respectively, of the background; scanning the black and white-sides of the stored image, the scan measuring a gray-scale value of scanned medium detected along a length of the syringe to generate feature vectors of the white-side scan and the black-side scan; low-pass filtering the feature vectors of the white and black-side scans to form a low-pass filtered scan; and analyzing a change in slope of the white-side scan, which represents a top scan line, for a point where the slope change exceeds a predetermine threshold, the point representing the air-liquid interface for the liquid in the container.

29. The method of claim 28, where the at least one operation further includes: calculating a position of a plunger of the syringe by performing the steps of: detecting a backside of the plunger; correcting the plunger position by subtracting an offset that corresponds to an actual thickness of the plunger; and calculating the volume of the liquid in the syringe based on the position of the air-liquid interface and the plunger position.

30. The method of claim 23, further including the steps of inputting a type of container that is being filled and determining the number and dimensions of the measurement areas that are overlaid on the stored image based on the inputted information.

31. The method of claim 20, wherein the container is a syringe with a slideable plunger and the step of performing at least one operation on the stored image comprises the steps of: calculating a position of the plunger by performing the step of: detecting a backside of the plunger; correcting the plunger position by subtracting an offset that corresponds to an actual thickness of the plunger; and calculating the volume of the liquid in the syringe as being a difference between the plunger position and a liquid level calculation in the syringe.

32. The method of claim 20, further including the steps of: performing a calibration of the container by: capturing an image of an empty container that includes graduations for indicating a volume of a content of the container; determining and recording pixel locations of each graduations on the container so as to equate each pixel location of the captured image with a corresponding volumetric measurement.

33. The method of claim 32, wherein the step of determining and recording pixel locations of each graduations on the container comprises the steps of: recording pixel data from the captured image; and fitting the pixel data to a $2^{nd}$ degree polynomial and determining associated coefficients to generate a curve that calibrates pixel position to plunger position in milliliter units.

34. A system for calculating a volume of liquid that is disposed within a container comprising: an imaging device that captures and stores an image of at least the volume of liquid in the container; a bifurcated background disposed behind the container so that at least the volume of liquid in the container is disposed in front of the background, wherein the container is constructed so that optical properties thereof and the liquid filled therein serve to define a liquid cylindrical lens causing a portion of the bifurcated background that lies behind the liquid in the container to be inverted in the captured and stored image; and a processor that performs at least one operation on the stored image including analyzing a location of the inverted portion relative to adjacent portions of the stored image to calculate the volume of the liquid within the container.

35. The system of claim 34, wherein the background is defined by a first region that has a black color and a second region that has a white color, wherein the at least one operation includes: dividing the stored image into a black-side and a white-side that correspond to the black and white-sides, respectively, of the background; scanning the black and white-sides of the stored image, the scan measuring a gray-scale value of scanned medium detected along a length of the container to generate feature vectors of the white-side scan and the black-side scan; low-pass filtering the feature vectors of the white and black-side scans to form a low-pass filtered scan; and analyzing a change in slope of the white-side scan, which represents a top scan line, for a point where the slope change exceeds a predetermine threshold, the point representing the air-liquid interface for the liquid in the container.

36. The system of claim 35, wherein the container is a syringe having a plunger and wherein the at least one operation further includes: calculating a position of the plunger by performing the steps of: detecting a backside of the plunger; correcting the plunger position by subtracting an offset that corresponds to an actual thickness of the plunger; and calculating the volume of the liquid in the syringe based on the position of the air-liquid interface and the plunger position.

37. The system of claim 34, wherein the imaging device comprises a digital camera and the system is incorporated into an automated medication preparation system including preparation and dispensing of medication to the container, the preparation system includes an automated device for preparing and dispensing a prescribed unit dose of medication, wherein the imaging device is located downstream of the automated device and the processor compares an inputted volume of a unit dose of medication that is to be delivered to the container with the volume of liquid that is actually disposed within the container as calculated by the processor in order to determine whether an underfill of overfill condition exists.

38. The system of claim 34, wherein the container is disposed between a digital camera and the background that is defined by a first region that has a first color contrast and a second region that has a second color contrast, with the first color contrast being substantially darker than the second color contrast, the stored image being defined by a set of vertical pixel numbers and a set of horizontal pixel numbers.

* * * * *